US012726698B1

(12) United States Patent
Murali

(10) Patent No.: US 12,726,698 B1
(45) Date of Patent: Sep. 1, 2026

(54) APPARATUS FOR AND METHOD OF CONTROLLING VISUALIZATION OF ANATOMICAL IMAGE DATA

(71) Applicant: PRAJNA LABS LLC, Andover, MA (US)

(72) Inventor: Ashwin Murali, Boston, MA (US)

(73) Assignee: Prajna Labs LLC, Andover, MA (US)

( * ) Notice: Subject to any disclaimer, the term of this patent is extended or adjusted under 35 U.S.C. 154(b) by 0 days.

(21) Appl. No.: 19/549,951

(22) Filed: Feb. 25, 2026

(51) Int. Cl.
*H04N 23/60* (2023.01)
*A61B 5/00* (2006.01)
*G06V 10/26* (2022.01)
*H04N 23/62* (2023.01)

(52) U.S. Cl.
CPC ............. *H04N 23/64* (2023.01); *A61B 5/742* (2013.01); *G06V 10/26* (2022.01); *H04N 23/62* (2023.01); *G06V 2201/03* (2022.01)

(58) Field of Classification Search
CPC ...................................................... H04N 23/64
See application file for complete search history.

(56) References Cited

U.S. PATENT DOCUMENTS

| | | | |
|---|---|---|---|
| 2022/0249178 A1 | 8/2022 | Charles et al. | |
| 2024/0007734 A1* | 1/2024 | Mikawa ............... | H04N 23/695 |
| 2024/0404075 A1* | 12/2024 | Lu .......................... | G06T 13/40 |
| 2025/0193514 A1* | 6/2025 | Connor ................ | A61B 5/0077 |

FOREIGN PATENT DOCUMENTS

| | | |
|---|---|---|
| CN | 117135439 A | 11/2023 |
| WO | 2024118995 A1 | 6/2024 |
| WO | 2025122379 A1 | 6/2025 |

OTHER PUBLICATIONS

Liu Z et al A Neural Representation Framework with LLM-Driven Spatial Reasoning for Open-Vocabulary 3D Visual Grounding arXiv:2507.06719v1 [cs.CV] Jul. 9, 2025.

* cited by examiner

*Primary Examiner* — Y Lee
(74) *Attorney, Agent, or Firm* — CALDWELL LLC

(57) ABSTRACT

An apparatus for and method of controlling visualization of anatomical image data are disclosed. The apparatus includes a processor and a memory containing instructions that configure the processor to receive imaging data and a user instruction, and generate, using a large language model (LLM), a proposed camera configuration based on the user instruction and imaging data. The apparatus simulates a camera view based on the proposed camera configuration and determines whether it satisfies visualization criteria. If not, the apparatus generates revised camera configurations using the LLM and simulates revised camera views. If the criteria are satisfied, the apparatus outputs the camera view corresponding to the proposed camera configuration, thereby facilitating efficient and effective visualization of anatomical image data.

20 Claims, 11 Drawing Sheets

APPARATUS FOR AND METHOD OF CONTROLLING VISUALIZATION OF ANATOMICAL IMAGE DATA

FIELD OF THE INVENTION

The present invention generally relates to the field of medical imaging. In particular, the present invention is directed to an apparatus for and method of controlling visualization of anatomical image data.

BACKGROUND

Visualization of anatomical imaging data is commonly used in clinical, research, and procedural contexts to inspect anatomical structures and guide decision-making. Existing visualization systems often rely on manual control and intervention, which can be inefficient and require substantial user expertise. Accordingly, there exists a need for improved systems and methods that reduce such inefficiencies and facilitate more effective and intuitive visualization of anatomical imaging data.

SUMMARY OF THE DISCLOSURE

In some aspects, the techniques described herein relate to an apparatus for controlling visualization of anatomical image data. The apparatus includes at least a processor, and a memory communicatively connected to the at least a processor, wherein the memory contains instructions configuring the at least a processor to receive imaging data, receive, through a user interface, a user instruction associated with the imaging data, generate, using a large language model (LLM), one or more LLM outputs as a function of the user instruction and the imaging data, wherein the one or more LLM outputs includes a proposed camera configuration, simulate a camera view as a function of the proposed camera configuration and the imaging data, determine whether the simulated camera view satisfies one or more visualization criteria associated with the user instruction, in response to determining that the simulated camera view does not satisfy the one or more visualization criteria generate, using the LLM, one or more revised camera configurations, and simulate corresponding revised camera views as a function of the one or more revised camera configurations, and in response to determining that the simulated camera view satisfies the one or more visualization criteria, output the camera view corresponding to the proposed camera configuration.

In some aspects, the techniques described herein relate to a method of controlling visualization of anatomical image data. The method includes receiving, using at least a processor, imaging data, receiving, using the at least a processor and through a user interface, a user instruction associated with the imaging data, generating, using the at least a processor and a large language model (LLM), one or more LLM outputs as a function of the user instruction and the imaging data, wherein the one or more LLM outputs includes a proposed camera configuration, simulating, using the at least a processor, a camera view as a function of the proposed camera configuration and the imaging data, determining, using the at least a processor, whether the simulated camera view satisfies one or more visualization criteria associated with the user instruction, in response to determining that the simulated camera view does not satisfy the one or more visualization criteria generating, using the at least a processor and the LLM, one or more revised camera configurations, and simulating, using the at least a processor, corresponding revised camera views as a function of the one or more revised camera configurations, and in response to determining that the simulated camera view satisfies the one or more visualization criteria, outputting, using the at least a processor, the camera view corresponding to the proposed camera configuration.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatuses for and methods of controlling visualization of anatomical image data. The apparatus includes at least a processor, and a memory communicatively connected to the at least a processor, wherein the memory contains instructions configuring the at least a processor to receive imaging data, receive, through a user interface, a user instruction associated with the imaging data, generate, using a large language model (LLM), one or more LLM outputs as a function of the user instruction and the imaging data, wherein the one or more LLM outputs includes a proposed camera configuration, simulate a camera view as a function of the proposed camera configuration and the imaging data, determine whether the simulated camera view satisfies one or more visualization criteria associated with the user instruction, in response to determining that the simulated camera view does not satisfy the one or more visualization criteria generate, using the LLM, one or more revised camera configurations, and simulate corresponding revised camera views as a function of the one or more revised camera configurations, and in response to determining that the simulated camera view satisfies the one or more visualization criteria, output the camera view corresponding to the proposed camera configuration.

Aspects of the present disclosure can be used to control visualization of imaging data generated as a function of large language model outputs. Aspects of the present disclosure can also be used to prevent presentation or actuation of visualization outputs that do not satisfy visualization criteria derived from imaging data and spatial constraints. This is so, at least in part, because the apparatus simulates camera views from LLM-generated camera configurations and evaluates the simulated camera views against deterministic visualization criteria prior to output.

Aspects of the present disclosure allow for constrained and verifiable use of large language models within imaging-based visualization systems by selectively outputting, revising, or suppressing LLM outputs based on simulation-driven evaluation, thereby improving reliability, anatomical validity, and operational correctness of visualization control.

Exemplary embodiments illustrating aspects of the present disclosure are described below in the context of several specific examples.

Figure 1:
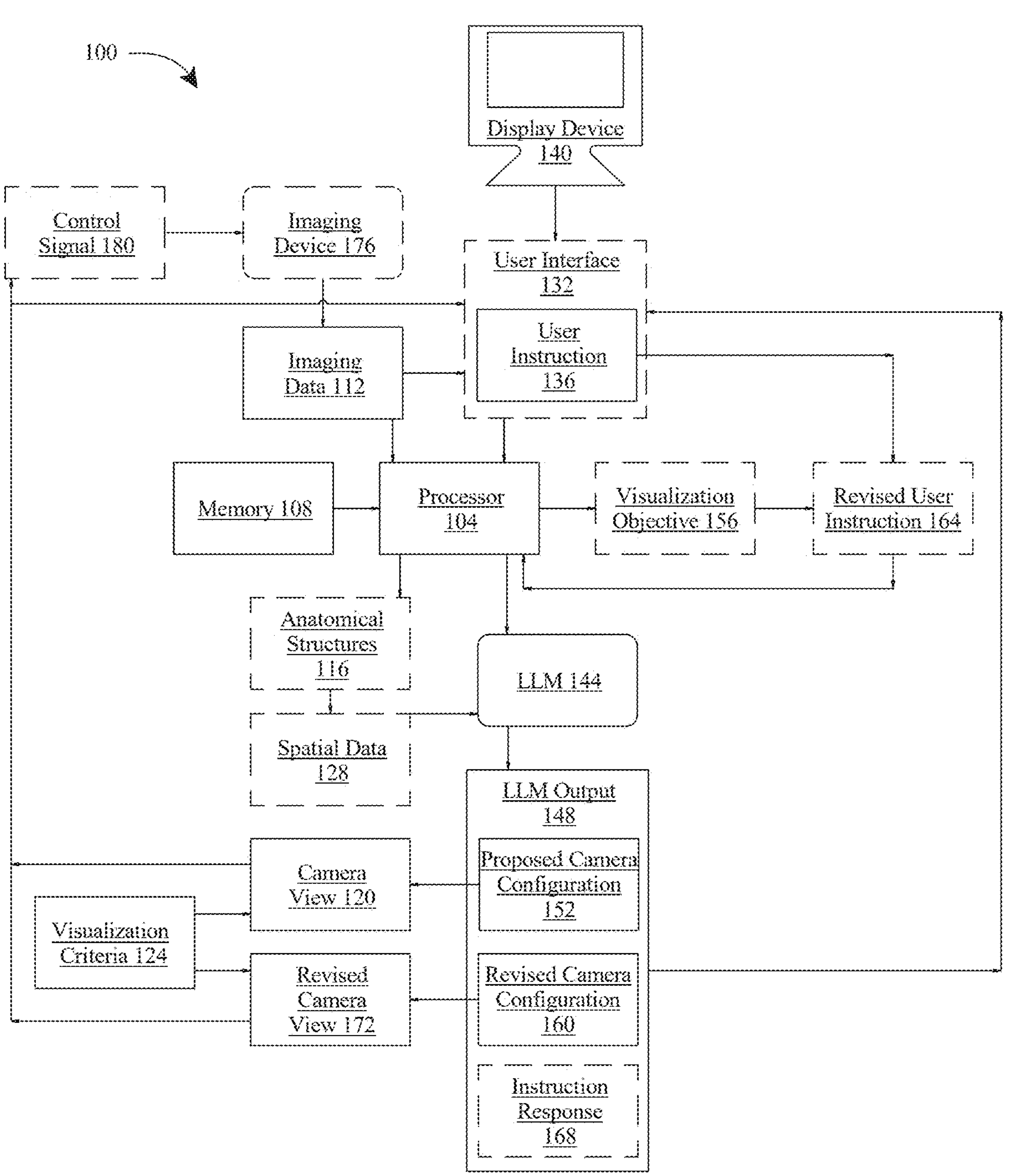
FIG. 1 illustrates a block diagram of an exemplary apparatus for controlling visualization of anatomical image data.

Referring now to FIG. 1, an exemplary embodiment of apparatus 100 for controlling visualization of anatomical image data is illustrated. Apparatus 100 may include circuitry such as without limitation a processor 104 communicatively connected to a memory 108; for instance, circuitry may include and/or be included in a computing device. Processor 104 may include any computing device as described in this disclosure, including without limitation a microcontroller, microprocessor, digital signal processor (DSP) and/or system on a chip (SoC) as described in this disclosure. Processor 104 may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented, as a non-limiting example, using a "shared nothing" architecture.

With continued reference to FIG. 1, memory 108 may include a primary memory and a secondary memory. "Primary memory" also known as "random access memory" (RAM) for the purposes of this disclosure is a short-term storage device in which information is processed. In one or more embodiments, during use of the computing device, instructions and/or information may be transmitted to primary memory wherein information may be processed. In one or more embodiments, information may only be populated within primary memory while a particular software is running. In one or more embodiments, information within primary memory is wiped and/or removed after the computing device has been turned off and/or use of a software has been terminated. In one or more embodiments, primary memory may be referred to as "Volatile memory" wherein the volatile memory only holds information while data is being used and/or processed. In one or more embodiments, volatile memory may lose information after a loss of power. "Secondary memory" also known as "storage," "hard disk drive" and the like for the purposes of this disclosure is a long-term storage device in which an operating system and other information is stored. In one or remote embodiments, information may be retrieved from secondary memory and transmitted to primary memory during use. In one or more embodiments, secondary memory may be referred to as non-volatile memory wherein information is preserved even during a loss of power. In one or more embodiments, data within secondary memory cannot be accessed by processor. In one or more embodiments, data is transferred from secondary to primary memory wherein processor 104 may access the information from primary memory.

With continued reference to FIG. 1, as used in this disclosure, "communicatively connected" means connected by way of a connection, attachment, or linkage between two or more relata such as without limitation electronic components, modules, and/or devices which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals there between may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, circuitry may alternatively or additionally be implemented by configuring a hardware device such as a combinatorial or sequential logic circuit, an application-specific integrated circuit (ASIC), a field-programmable gate array (FPGA), or other hardware unit; memory may be attached thereto to further configure the hardware unit using read-only memory (ROM) or any other static or writable memory as described in this disclosure. Alternatively or additionally, hardware units and/or modules may be combined with and/or in communication with a processor, such as without limitation in a system-on-chip architecture wherein some functions are configured by modification or design of hardware circuitry, such as without limitation FPGA circuitry, while others are configured in the form of instructions in memory for one or more processors. As a non-limiting example, any step or combination of steps described herein may be performed entirely using hardware circuit configured to perform such steps either with static memory or rewritable memory. Such steps or combinations of steps may include signing with a digital signature, cryptographically hashing, evaluation of zero-knowledge proofs, or any other specific process described in this disclosure.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, processor 104 is configured to receive imaging data 112. For the purposes of this disclosure, "imaging data" is digital data representing spatial, structural, or volumetric characteristics of a subject. As a non-limiting example, imaging data 112 may include data indexed to two-dimensional coordinate systems, three-dimensional coordinate systems, or higher-dimensional coordinate systems incorporating time, phase, or modality dimensions. As another non-limiting example, imaging data 112 may include discrete samples, continuous fields, or hybrid representations derived from sensor acquisition or computational reconstruction. In some embodiments, imaging data 112 may include data acquired using one or more medical imaging modalities. As a non-limiting example, imaging data 112 may include computed tomography (CT) data representing X-ray attenuation values spatially distributed across a subject, magnetic resonance imaging (MRI) data representing signal intensities derived from magnetic resonance interactions within tissue, or ultrasound imaging data representing reflected acoustic signals. As another non-limiting example, imaging data 112 may include angiographic imaging data, fluoroscopic imaging data, positron emission tomography (PET) data, single-photon emission computed tomography (SPECT) data, optical coherence tomography data, intravascular imaging data, endoscopic imaging data, or combinations thereof. In some embodiments, imaging data 112 may further include reconstructed, reformatted, or derived representations generated from such modalities, including volumetric datasets, multi-planar reconstructions, projection images, or time-varying image sequences. As a non-limiting example, imaging data 112 may include pixel-based representations, voxel-based representations, point-based representations, mesh-based representations, or combinations thereof. As another non-limiting example, imaging data 112 may include surface representations, volumetric representations, or topological representations encoding spatial relationships between regions of the subject. As a non-limiting example, imaging data 112 may include data acquired directly from one or more sensors, data reconstructed from sensor measurements, or data generated algorithmically to approximate or predict spatial characteristics of the subject. As another non-limiting example, imaging data 112 may include simulated data, interpolated data, extrapolated data, or generatively produced data. As a non-limiting example, imaging data 112 may include intensity values, gradient values, flow values, deformation values, confidence values, probability values, categorical labels, or embeddings, each associated with one or more spatial positions. As another non-limiting example, imaging data 112 may include segmentation outputs, boundary representations, distance fields, anatomical label maps, or graph structures encoding spatial relationships.

With continued reference to FIG. 1, in some embodiments, imaging data 112 may be associated with at least an anatomical structure 116. For the purposes of this disclosure, "anatomical structure" is a biological structure of a subject. As a non-limiting example, anatomical structure 116 may include a cardiac chamber, a heart valve, a blood vessel, a coronary artery, a pulmonary vein, a vena cava, or an aortic root. As another non-limiting example, anatomical structure 116 may include a brain region, a ventricle, a cranial nerve, a spinal cord region, a vertebral body, or a cerebrovascular structure. As another non-limiting example, anatomical structure 116 may include a lung lobe, a bronchial segment, an airway lumen, or a pleural boundary. As a non-limiting example, anatomical structure 116 may include a gastrointestinal structure including a stomach region, an intestinal lumen, a colon segment, a biliary duct, or a pancreatic duct. As another non-limiting example, anatomical structure 116 may include a urological structure including a kidney, a ureter segment, a bladder region, or a prostate region. As another non-limiting example, anatomical structure 116 may include a musculoskeletal structure including a bone, a joint space, a cartilage region, a tendon, or a ligament. As a non-limiting example, anatomical structure 116 may include a lesion, a tumor region, a cyst, a clot, a plaque region, or a stenosis region represented within imaging data 112. As another non-limiting example, anatomical structure 116 may include a boundary region, a lumen region, a wall region, a tissue interface region, or a region of interest derived from segmentation operations performed on imaging data 112.

With continued reference to FIG. 1, in some embodiments, receiving the imaging data 112 may include parsing imaging metadata and normalizing imaging data 112 into a standardized coordinate representation used for simulation and rendering. As a non-limiting example, normalization may include resampling voxel spacing to a target spacing, aligning axes to a standard anatomical orientation, and mapping intensity values into normalized ranges for display. In some embodiments, receiving the imaging data 112 may include performing artifact reduction, denoising, or intensity correction operations prior to downstream segmentation or simulation. As a non-limiting example, artifact reduction may include metal artifact correction for CT imaging and bias-field correction for MRI imaging. In some embodiments, the preprocessing pipeline may generate intermediate representations stored in the memory 108, including downsampled volumes, multi-resolution pyramids, and region-of-interest crops. As a non-limiting example, the processor 104 may create a low-resolution representation used for rapid initial simulation of the camera view 120 and a high-resolution representation used for final output after visualization criteria 124 are satisfied.

With continued reference to FIG. 1, in some embodiments, receiving the imaging data 112 may include identifying one or more anatomical structures 116 within the imaging data 112. In some embodiments, identifying one or more anatomical structures 116 may include executing one or more segmentation operations configured to assign anatomical labels to pixels, voxels, points, or regions within the imaging data 112. In some embodiments, identifying one or more anatomical structures 116 within imaging data 112 may include executing a segmentation module comprising one or more machine learning models and one or more post-processing operations. As a non-limiting example, the segmentation module may include a first model configured to segment major anatomical structures and a second model configured to segment finer substructures within a region of interest. In some embodiments, a segmentation model may include a three-dimensional convolutional network configured to ingest volumetric patches and output per-voxel segmentation logits for multiple anatomical classes. As a non-limiting example, the segmentation model may include an encoder path configured to extract hierarchical features at multiple spatial scales and a decoder path configured to reconstruct full-resolution segmentation outputs. In some embodiments, the segmentation model may be trained using training data comprising paired imaging data and ground-truth segmentation labels. As a non-limiting example, training data may include CT volumes with expert-labeled chamber boundaries, MRI volumes with expert-labeled vessel boundaries, and ultrasound sequences with expert-labeled lumens. In some embodiments, sources of segmentation training data may include curated clinical imaging repositories, licensed medical imaging datasets, public medical imaging datasets, and internally generated datasets labeled under clinician supervision. As a non-limiting example, the training data may include multi-institution imaging data aggregated to increase robustness across scanner types and acquisition protocols. In some embodiments, segmentation model training may include augmentation operations configured to increase model generalization. As a non-limiting example, augmentation may include random rotations, random scaling, simulated noise injection, intensity jitter, simulated motion blur, or simulated artifacts consistent with real clinical acquisition conditions. In some embodiments, the segmentation module may generate confidence values associated with segmented regions, and the apparatus 100 may use confidence values to select whether to trust a segmented region for spatial data 128 generation. As a non-limiting example, a region with low segmentation confidence may be excluded from adjacency computations or treated as uncertain during evaluation of visualization criteria 124.

With continued reference to FIG. 1, in some embodiments, receiving the imaging data 112 may include generating spatial data 128 as a function of the one or more anatomical structures 116, wherein the spatial data 128 may include one or more segmented regions associated with one or more anatomical structures 116. For the purposes of this disclosure, "spatial data" is structured data representing spatial properties or relationships associated with one or more anatomical structures. As a non-limiting example, spatial data 128 includes segmented regions, region boundaries, region centroids, bounding volumes, adjacency relationships, coordinate sets, or spatial constraints. for the purposes of this disclosure, "segmented regions" associated with one or more anatomical structures are spatially delineated portions of imaging data that are identified as corresponding to specific anatomical structures. In some cases, segmented regions may be distinguished from surrounding portions of the imaging data based on assigned labels or boundaries. As a non-limiting example, segmented regions associated with one or more anatomical structures may include contiguous groups of pixels, voxels, points, or surface elements that have been assigned a common anatomical label by a segmentation operation. As another non-limiting example, segmented regions may include volumetric regions representing an organ, lumen regions representing internal cavities, boundary regions representing interfaces between tissues, or surface regions representing anatomical walls. In some embodiments, segmented regions associated with one or more anatomical structures may be represented using one or more spatial representations, including binary masks, multi-class label maps, probability maps, surface meshes, point clouds, or distance fields. As a non-limiting example, a segmented region may be represented as a voxel-wise label map aligned with imaging data 112 or as a surface mesh derived from boundary extraction. In some embodiments, segmented regions associated with one or more anatomical structures may include associated metadata describing geometric, spatial, or relational properties. As a non-limiting example, such metadata may include region volume, surface area, centroid location, principal axes, adjacency relationships with other segmented regions, or confidence values indicating segmentation reliability.

With continued reference to FIG. 1, in some embodiments, generating spatial data 128 may include generating one or more segmented regions by applying a segmentation model to imaging data 112. In some embodiments, generating spatial data 128 may include deriving a graph representation of anatomical structures 116 and their relationships. As a non-limiting example, nodes of the graph may correspond to anatomical structures 116 and edges may correspond to adjacency, connectivity, containment, or proximity relationships derived from segmented regions. In some embodiments, generating spatial data 128 may include computing geometric primitives used for camera placement, including centroids, principal axes, boundary surfaces, bounding volumes, and navigable cavity volumes. As a non-limiting example, a principal axis of an elongated vessel may be computed by principal component analysis of voxel coordinates within a segmented vessel region. In some embodiments, generating spatial data 128 may include computing a set of spatial constraints used for physical realizability evaluation. As a non-limiting example, a spatial constraint may define a forbidden region outside an anatomical lumen and a permitted region within the lumen, enabling the processor 104 to determine whether a camera position is physically realizable. In some embodiments, spatial constraints may be computed using signed distance fields derived from segmented region boundaries. As a non-limiting example, a signed distance field may assign negative values to locations inside a segmented cavity and positive values to locations outside the cavity, enabling rapid collision and intersection checks during simulation.

With continued reference to FIG. 1, the processor 104 is configured to receive, through a user interface 132, a user instruction 136 associated with the imaging data 112. For the purposes of this disclosure, "user instruction" is an input expressing a desired visualization, navigation, or inspection operation associated with imaging data. As a non-limiting example, the user instruction 136 may include a natural-language request specifying a target anatomical structure and a desired viewpoint or viewing objective. As a non-limiting example, the user instruction 136 may include a natural-language request specifying a target anatomical structure and a desired viewpoint or viewing objective. As another non-limiting example, the user instruction 136 may include a request to position a camera view 120 inside, around, or relative to an anatomical structure 116, such as requesting an internal view, an external overview, or a boundary-focused inspection of the anatomical structure 116. As a non-limiting example, the user instruction 136 may include a request to visualize an anatomical structure 116 from a specified orientation, direction, or anatomical reference frame, such as requesting an anterior view, posterior view, superior view, inferior view, or oblique view. As another non-limiting example, the user instruction 136 may include a request to center, highlight, or emphasize a particular anatomical structure 116 or region of interest within the imaging data 112. As a non-limiting example, the user instruction 136 may include a request to navigate through a lumen, cavity, or pathway represented within the imaging data 112, including requests to advance, retract, rotate, or adjust a simulated camera view 120 along a path defined by an anatomical structure 116. As another non-limiting example, the user instruction 136 may include a request to inspect a junction, bifurcation, narrowing, or abnormality associated with an anatomical structure 116. As a non-limiting example, the user instruction 136 may include a request to compare multiple camera views 120, to adjust a field-of-view parameter, to zoom in or zoom out, or to switch between different visualization modes, including volumetric rendering, surface rendering, or cross-sectional views. As another non-limiting example, the user instruction 136 may include a request to generate an explanatory or descriptive response associated with a camera view 120, including textual output describing visible anatomical structures 116 or spatial relationships therebetween. As a non-limiting example, the user instruction 136 may be provided as spoken input, typed text, gesture input, touch input, or selection of a graphical control element displayed within the user interface 132.

With continued reference to FIG. 1, the apparatus 100 may include a display device 140 and a user interface 132. For the purposes of this disclosure, "display device" is a hardware component configured to present visual information to a user. As a non-limiting example, the display device 140 may include a computer monitor, a touchscreen display, a tablet display, a mobile device screen, a head-mounted display, smart glasses, an augmented reality display, a virtual reality display, a heads-up display, or a projector. As another non-limiting example, the display device 140 may include a stereoscopic display configured to present three-dimensional visual content. For the purposes of this disclosure, a "user interface" is a means by which a user and a computer system interact. For example through the use of input devices and software. A user interface 132 may include a graphical user interface (GUI), command line interface (CLI), menu-driven user interface, touch user interface, voice user interface (VUI), form-based user interface, any combination thereof and the like. In some embodiments, user interface 132 may operate on and/or be communicatively connected to a decentralized platform, metaverse, and/or a decentralized exchange platform associated with the user. For example, a user may interact with user interface 132 in virtual reality. In some embodiments, a user may interact with the user interface 132 using a computing device distinct from and communicatively connected to at least a processor 104. For example, a smart phone, smart, tablet, or laptop operated by a user. In an embodiment, user interface 132 may include a graphical user interface. A "graphical user interface," as used herein, is a graphical form of user interface that allows users to interact with electronic devices. In some embodiments, GUI may include icons, menus, other visual indicators or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run program, and the like because clicking on them yields instant access. As a non-limiting example, the user interface 132 may include a graphical user interface, a voice interface, or a multimodal interface. As a non-limiting example, the user interface 132 may include a graphical user interface comprising one or more visual elements displayed on the display device 140, including menus, sliders, buttons, icons, overlays, or annotations associated with imaging data 112 and camera views 120. As another non-limiting example, the user interface 132 may include a voice-based interface configured to receive spoken user instructions 136 and to present audio responses. As a non-limiting example, the user interface 132 may include a multimodal interface combining multiple input and output modalities. As another non-limiting example, the user interface 132 may include a touch-sensitive interface configured to receive gesture input, a pointer-based interface configured to receive mouse or stylus input, or a spatial interface configured to receive head-movement, eye-tracking, or hand-tracking input.

With continued reference to FIG. 1, in some embodiments, receiving the user instruction 136 may include converting voice input to text using a speech recognition pipeline executed by the processor 104 prior to passing content to large language model (LLM) 144. In some embodiments, the speech recognition pipeline may include an acoustic model configured to convert audio waveforms into phonetic representations and a language model configured to convert the phonetic representations into textual tokens corresponding to the user instruction 136. In some embodiments, converting voice input to text may include performing noise reduction, echo cancellation, or voice activity detection on the audio input prior to transcription. As a non-limiting example, the processor 104 may apply a noise suppression model to reduce background noise and isolate speech segments before executing speech-to-text conversion. In some embodiments, receiving the user instruction 136 may include performing terminology normalization on the textual representation of the user instruction 136 prior to passing the content to the LLM 144. In some embodiments, terminology normalization may include mapping synonyms, abbreviations, acronyms, and colloquial anatomical phrases into canonical anatomical terms corresponding to anatomical structure 116 labels represented within spatial data 128. In some embodiments, the processor 104 may perform terminology normalization using a vocabulary mapping module configured to reference a controlled anatomical vocabulary stored in the memory 108. As a non-limiting example, the controlled anatomical vocabulary may include standardized anatomical names, aliases, abbreviations, and hierarchical relationships between anatomical structures 116. In some embodiments, terminology normalization may include tokenizing the user instruction 136 into individual words or phrases and comparing the tokens against entries in the controlled anatomical vocabulary. As a non-limiting example, the processor 104 may replace informal phrases or shorthand expressions appearing in the user instruction 136 with corresponding canonical anatomical terms prior to providing the normalized user instruction 136 to the LLM 144. In some embodiments, terminology normalization may further include resolving grammatical variations, plurality, or anatomical orientation descriptors present in the user instruction 136. As a non-limiting example, the processor 104 may normalize variations of directional descriptors into standardized orientation labels used by downstream visualization logic. In some embodiments, the processor 104 may generate and store both an original representation and a normalized representation of the user instruction 136 in the memory 108. As a non-limiting example, the original representation may be retained for audit or user feedback purposes, while the normalized representation may be used as an input to the LLM 144 for generating one or more LLM outputs 148, including proposed camera configurations 152.

With continued reference to FIG. 1, in some embodiments, receiving the user instruction 136 may include evaluating, using the LLM 144, the user instruction 136 to determine whether the user instruction 136 defines a visualization configuration as a function of the spatial data 128. For the purposes of this disclosure, "visualization configuration" is a set of parameters defining how imaging data 112 is to be visually presented. In some cases, visualization configuration may include at least one parameter corresponding to camera placement, camera orientation, viewing direction, field of view, zoom level, or target anatomical structure 116. In some embodiments, evaluating the user instruction 136 may include parsing the user instruction 136 to identify anatomical phrases, spatial descriptors, and viewing intent indicators. As a non-limiting example, the processor 104 may tokenize the user instruction 136 and identify tokens corresponding to anatomical structures 116, directional terms, relational terms, or viewing qualifiers.

With continued reference to FIG. 1, in some embodiments, evaluating the user instruction 136 may further include mapping the identified anatomical phrases (e.g., anatomical feature) to anatomical structures 116 represented within the spatial data 128. As a non-limiting example, the processor 104 may compare anatomical terms (e.g., anatomical feature) extracted from the user instruction 136 against labels, identifiers, or metadata associated with segmented regions included in the spatial data 128. In some embodiments, determining whether the user instruction 136 defines the visualization configuration may include evaluating whether the mapped anatomical structures 116 and associated descriptors provide sufficient information to determine one or more camera parameters. As a non-limiting example, the processor 104 may determine whether the user instruction 136 specifies or implies a target anatomical structure 116, a relative viewing position, or a desired viewing orientation sufficient to generate the proposed camera configuration 152. In some embodiments, evaluating the user instruction 136 may include generating an internal representation of required visualization parameters and comparing the internal representation against a set of required parameters for camera configuration generation. As a non-limiting example, the processor 104 may determine that the user instruction 136 defines a visualization configuration when the internal representation includes at least a target anatomical structure 116 and a spatial relationship relative to that anatomical structure 116. In some embodiments, when the evaluation indicates that the user instruction 136 does not define the visualization configuration, the processor 104 may determine that additional information is required to resolve ambiguity or incompleteness. As a non-limiting example, the processor 104 may identify missing parameters related to camera position, viewing direction, or anatomical scope and may trigger downstream logic for determining a visualization objective 156 or generating a revised user instruction 164. In some embodiments, evaluating the user instruction 136 using the LLM 144 may include conditioning the LLM 144 on the spatial data 128 or summaries thereof. As a non-limiting example, the processor 104 may provide the LLM 144 with a list of available anatomical structures 116, spatial relationships, or constraints derived from the spatial data 128 to enable the LLM 144 to assess whether the user instruction 136 is resolvable within the context of the available imaging data 112. In some embodiments, the processor 104 may store the evaluation result indicating whether the user instruction 136 defines the visualization configuration in the memory 108. As a non-limiting example, the evaluation result may be used to control whether the processor 104 proceeds directly to generating the proposed camera configuration 152 or initiates additional clarification, inference, or revision steps.

With continued reference to FIG. 1, in some embodiments, in response to determining that the user instruction 136 does not define the visualization configuration, the processor 104 may determine a visualization objective 156 as a function of historical data associated with prior visualization configurations and/or prior user instructions. For the purposes of this disclosure, "visualization objective" is a representation of an intended visualization outcome. In some cases, visualization objective 156 may be expressed in terms of spatial, anatomical, or contextual goals. As a non-limiting example, historical data may include previously accepted camera configurations, previously successful camera views, interaction sequences, navigation trajectories, or session context data stored in the memory 108. In some embodiments, determining a visualization objective 156 may include selecting among multiple candidate objectives based on historical data associated with prior visualization configurations. As a non-limiting example, candidate objectives may include maximizing the number of connected anatomical structures visible from a target location, centering a target feature, or maintaining a stable orientation relative to a reference axis. In some embodiments, historical data may include camera configuration sequences that were previously accepted by a user, including time-ordered camera position vectors and orientation vectors. As a non-limiting example, the apparatus 100 may learn that a user prefers a wider field-of-view parameter and may incorporate that preference into the visualization objective 156. As a non-limiting example, the processor 104 may retrieve historical camera configurations that were previously accepted by a user for similar anatomical structures 116 or similar user instructions 136 and extract common parameters, such as preferred camera distance, orientation, or field-of-view. The processor 104 may aggregate such historical parameters to infer a visualization objective 156 consistent with prior successful outcomes. As a non-limiting example, the processor 104 may analyze geometric properties of segmented regions, including centroids, principal axes, curvature, adjacency relationships, or lumen directionality, and may define a visualization objective 156 that prioritizes alignment of the camera view 120 with a principal anatomical axis or maximization of visible boundary regions. As a non-limiting example, the processor 104 may prompt the LLM 144 to generate one or more candidate visualization objectives based on the user instruction 136 and available spatial data 128, such as "center the largest connected lumen," "maximize visibility of branching regions," or "maintain continuity with a prior camera view 120." The processor 104 may then select among the candidate visualization objectives based on predefined selection criteria, including feasibility, relevance, or consistency with historical data. in some embodiments, the processor 104 may quantify a visualization objective 156 using one or more objective functions or scoring functions. As a non-limiting example, an objective function may assign weights to visibility metrics, framing metrics, or physical realizability metrics and compute a scalar score for a candidate camera configuration. The processor 104 may store the objective function parameters in the memory 108 and use the objective function to evaluate proposed and revised camera configurations 160 during iterative simulation. In some embodiments, determining the visualization objective 156 may include incorporating system-level constraints or preferences. As a non-limiting example, the processor 104 may define a visualization objective 156 that limits camera motion between successive views to reduce disorientation, enforces a minimum distance from anatomical boundaries to avoid unrealistic perspectives, or prioritizes stable orientations aligned with a reference anatomical frame. In some embodiments, the processor 104 may determine the visualization objective 156 dynamically during an interaction session. As a non-limiting example, the processor 104 may update the visualization objective 156 in response to user feedback, acceptance or rejection of prior camera views 120, or changes in the user instruction 136. The processor 104 may store successive visualization objectives 156 in the memory 108 and use them to guide adaptive refinement of camera configurations across multiple interaction cycles.

With continued reference to FIG. 1, in some embodiments, the processor 104 may generate a revised user instruction 164 as a function of the visualization objective 156. For the purposes of this disclosure, "revised user instruction" is a modified user instruction configured to guide generation of a visualization configuration. As a non-limiting example, the revised user instruction 164 may include additional constraints specifying a target structure, a desired orientation, or a desired framing of the camera view 120. In some embodiments, generating the revised user instruction 164 as a function of the visualization objective 156 may include generating a clarification prompt through the user interface 132. As a non-limiting example, a clarification prompt may request a selection between two candidate targets or request confirmation of whether to prioritize viewing a primary anatomical structure or additional connected structures. In some embodiments, generating the revised user instruction 164 may include automatically appending constraints inferred from session context to reduce underconstraint. As a non-limiting example, if a prior camera view 120 was inside a known cavity, the revised user instruction 164 may incorporate that cavity as a default starting context for the next proposed camera configuration 152.

With continued reference to FIG. 1, the processor 104 is configured to generate, using a LLM 144, one or more LLM outputs 148 as a function of the user instruction 136 and the imaging data 112, wherein the one or more LLM outputs 148 includes a proposed camera configuration 152. A "large language model," as used herein, is a deep learning data structure that can recognize, summarize, translate, predict, and/or generate text and other content based on knowledge gained from large-scale datasets. Large language models 144 may be trained on large sets of data. Training sets may be drawn from diverse sets of data such as, as non-limiting examples, anatomical descriptions, medical imaging reports, procedural documentation, visualization instructions, navigation logs, camera configuration records, simulation outcomes, and user interaction histories associated with imaging systems. In some embodiments, training sets may include a variety of subject matters, such as, as non-limiting examples, radiology reports, surgical planning documents, anatomical atlases, imaging protocol descriptions, clinician-authored visualization instructions, and records of accepted and rejected camera views. In some embodiments, training sets of an LLM 144 may include information from one or more public or private databases. As a non-limiting example, training sets may include databases associated with medical imaging systems, anatomical knowledge bases, or visualization platforms. In some embodiments, training sets may include portions of documents correlated to examples of camera configurations, visualization criteria satisfaction, or simulation-based validation outcomes. In an embodiment, an LLM 144 may include one or more architectures based on capability requirements of the LLM 144. Exemplary architectures may include, without limitation, GPT (Generative Pretrained Transformer), BERT (Bidirectional Encoder Representations from Transformers), T5 (Text-To-Text Transfer Transformer), and the like. Architecture choice may depend on required capabilities such as generating proposed camera configurations 152, interpreting user instructions 136, or reasoning over spatial data 128.

With continued reference to FIG. 1, in some embodiments an LLM 144 may include and/or be produced using Generative Pretrained Transformer (GPT), GPT-2, GPT-3, GPT-4, and the like. An LLM 144 may include a text prediction-based algorithm configured to receive a sequence of tokens corresponding to a user instruction 136 and to generate one or more LLM outputs 148 based on learned probability distributions. As a non-limiting example, when a user instruction 136 includes phrases such as "show the interior of the vessel" or "look toward the branching region," the LLM 144 may predict subsequent tokens corresponding to a camera position, orientation, or viewing objective. An LLM 144 may output such predictions by ranking candidate outputs, including camera parameters, by likelihood or confidence. In some embodiments, an LLM 144 may include an encoder component and a decoder component.

With continued reference to FIG. 1, LLM 144 may include an attention mechanism utilizing a transformer architecture. An "attention mechanism," as used herein, is a part of a neural architecture that enables a system to dynamically prioritize relevant portions of input data. In the context of anatomical visualization, the attention mechanism may be applied to textual tokens corresponding to anatomical structures 116, spatial descriptors, viewing intent indicators, and prior camera configuration context. Applying an attention mechanism, LLM 144 may focus on relevant anatomical terms, spatial relationships, and feasibility constraints when generating proposed camera configurations 152 or revised camera configurations 160.

With continued reference to FIG. 1, LLM 144 may include a transformer architecture. In some embodiments, an encoder component of LLM 144 may include transformer architecture configured to process user instruction 136 tokens together with contextual inputs derived from spatial data 128. Transformer architecture may process the entire input sequence concurrently, enabling contextual reasoning across anatomical terms, spatial relationships, and visualization intent. Positional encoding may be used to preserve token ordering within the user instruction 136 and contextual prompts provided to the LLM 144.

With continued reference to FIG. 1, attention mechanisms may improve handling of longer or more complex user instructions 136 that include multiple anatomical references, navigation requests, or viewing constraints. Applying attention, LLM 144 may identify which anatomical structures 116, spatial descriptors, and constraints are most relevant for generating a proposed camera configuration 152. Context vectors generated by the attention mechanism may encode semantic relationships between anatomical terms and visualization objectives.

With continued reference to FIG. 1, attention mechanisms may include generalized attention, self-attention, multi-head attention, additive attention, global attention, and the like. In generalized attention, when a sequence of tokens representing a user instruction 136 is processed, LLM 144 may compare anatomical phrases against generated camera configuration outputs to determine relevance. In self-attention, LLM 144 may identify relationships between different anatomical references and spatial qualifiers within the same user instruction 136. In multi-head attention, LLM 144 may evaluate multiple interpretive perspectives simultaneously, including anatomical relevance, spatial feasibility, and consistency with prior camera views 120.

With continued reference to FIG. 1, multi-headed attention in an encoder may apply self-attention to associate anatomical terms, spatial descriptors, and visualization intent indicators. As a non-limiting example, LLM 144 may associate phrases such as "inside," "along," or "facing toward" with spatial relationships relevant to camera placement. Query, key, and value vectors may encode learned representations of anatomical structures 116, spatial data 128, and visualization criteria 124, enabling computation of attention weights used to generate proposed camera configurations 152.

With continued reference to FIG. 1, in order to use self-attention in a multi-headed attention computation, query, key, and value vectors may be split into multiple attention heads. Each head may focus on different aspects of the user instruction 136, such as anatomical target selection, orientation reasoning, physical realizability, or consistency with historical visualization outcomes. The combined output may represent a unified interpretation used to guide camera configuration generation.

With continued reference to FIG. 1, an encoder of the transformer may include residual connections and layer normalization to stabilize processing of user instruction 136 sequences. Such processing may improve robustness when interpreting complex or underspecified visualization requests.

With continued reference to FIG. 1, a decoder of the transformer architecture may generate outputs autoregressively. In some embodiments, the decoder may generate sequences corresponding to camera parameters, instruction responses 168, or revised user instructions 164. Autoregressive decoding enables the LLM 144 to generate coherent multi-parameter outputs conditioned on previously generated parameters and evaluation feedback. Decoder masking techniques may prevent conditioning on future tokens, ensuring consistent generation of camera configurations and instruction responses 168 based on prior context and spatial constraints.

With continued reference to FIG. 1, a second multi-headed attention layer in the decoder may attend to encoder outputs representing parsed user instruction 136 and spatial context derived from spatial data 128. This alignment enables coordination between anatomical intent and generated camera configuration parameters.

With continued reference to FIG. 1, outputs of decoder layers may be passed through a classifier layer to produce probability distributions over candidate outputs. As a non-limiting example, candidate outputs may include alternative camera orientations, camera positions, zoom levels, or textual descriptions of a camera view 120. Decoding may continue until a termination condition is met, such as generation of a complete proposed camera configuration 152 or instruction response 168. In some embodiments, decoder layers may be stacked to enable deeper reasoning about spatial relationships, visualization constraints, and prior simulation outcomes.

With continued reference to FIG. 1, in some embodiments, processor 104 may incorporate retrieval-augmented generation into LLM 144. Retrieved information may include anatomical reference data, spatial constraints, prior camera configurations, or visualization criteria definitions. Such retrieved data may ground LLM outputs 148 in authoritative anatomical and imaging knowledge and reduce generation of infeasible camera configurations.

With continued reference to FIG. 1, in some embodiments, similarity-based fetching may retrieve prior visualization sessions, accepted camera views, or anatomical descriptions most relevant to a current user instruction 136. Retrieved content may be provided to LLM 144 to improve consistency and suppress invalid outputs. In some embodiments, hypothetical document embeddings generated by LLM 144 may represent semantic interpretations of a user instruction 136 or candidate visualization objective 156. Such embeddings may be compared to stored embeddings associated with successful visualization outcomes.

With continued reference to FIG. 1, an LLM 144 may receive inputs comprising textual user instruction 136, spatial context summaries derived from spatial data 128, historical camera configuration data, or evaluation feedback from simulated camera views 120. Inputs may be received from a user device including an imaging workstation, a tablet, or a clinical console. LLM 144 may generate outputs including a proposed camera configuration 152, a revised camera configuration 160, or an instruction response 168. Textual outputs may describe camera placement, anatomical visibility, or satisfaction of visualization criteria 124.

With continued reference to FIG. 1, in some embodiments, an LLM 144 may be generally trained and subsequently specifically trained. Specific training may include training on anatomical navigation tasks, visualization instruction interpretation, camera configuration outcomes, and simulation-based validation results. Training data may include user instructions paired with accepted camera views, rejected camera views, and associated visualization criteria 124, and may be updated iteratively through feedback from simulation and user interaction outcomes.

With continued reference to FIG. 1, for the purposes of this disclosure, "large language model (LLM) output" is data generated by an LLM. In some cases, LLM outputs 148 may represent a proposed action, configuration, or response. As a non-limiting example, an LLM output 148 may include a proposed camera configuration 152 defining at least one of a camera position vector, a camera orientation vector, a zoom parameter, or a field-of-view parameter for visualizing imaging data 112. For the purposes of this disclosure, "proposed camera configuration" is a set of parameters defining a viewpoint for visualization. For the purposes of this disclosure, a "camera position vector" is a mathematical representation defining a location of a virtual camera within a coordinate space associated with imaging data 112. The camera position vector may specify a spatial point from which a camera view 120 is rendered relative to spatial data 128. For the purposes of this disclosure, a "camera orientation vector" is a mathematical representation defining an angular direction of a virtual camera within a coordinate space associated with imaging data 112. The camera orientation vector may determine an orientation of the camera view 120 relative to one or more axes of the spatial data 128. For the purposes of this disclosure, a "zoom parameter" is a value defining a magnification level applied to a camera view 120 relative to imaging data 112. The zoom parameter may control a scale at which anatomical structures 116 are displayed within the camera view 120. For the purposes of this disclosure, a "field-of-view parameter" is a value defining an angular extent of a scene captured by a virtual camera within a coordinate space associated with imaging data 112. The field-of-view parameter may determine a breadth of spatial content visible within the camera view 120.

With continued reference to FIG. 1, as another non-limiting example, an LLM output 148 may include a revised camera configuration 160 generated in response to determining that a simulated camera view fails to satisfy one or more visualization criteria 124. As another non-limiting example, an LLM output 148 may include a visualization objective 156 specifying a target anatomical structure 116, a desired viewpoint relative to the anatomical structure 116, or a constraint on visibility within a camera view 120. As another non-limiting example, an LLM output 148 may include an instruction response 168 configured to be presented via a user interface 132, wherein the instruction response 168 describes how the generated camera view 120 corresponds to the user instruction 136. As another non-limiting example, an LLM output 148 may include a revised user instruction 164 that refines, clarifies, or supplements the original user instruction 136 to enable generation of a physically realizable camera view 120 within spatial data 128.

With continued reference to FIG. 1, in some embodiments, the LLM 144 may be executed locally, executed on-premises, executed in a private cloud, executed in a public cloud, or executed in a hybrid deployment. As a non-limiting example, a privacy-preserving deployment may execute LLM inference within a restricted network boundary associated with clinical infrastructure. In some embodiments, generating one or more LLM outputs 148 may include constructing an instruction context for the LLM 144 comprising the user instruction 136 and an anatomical context derived from spatial data 128. As a non-limiting example, anatomical context may include a list of available anatomical structures 116, centroid locations, adjacency relationships, and constraint indicators describing navigable cavities. In some embodiments, generating one or more LLM outputs 148 may include providing the LLM 144 with simulation feedback derived from prior camera view 120 evaluations. As a non-limiting example, simulation feedback may include an indicator that a target anatomical feature is not visible, an indicator that a boundary region is occluded, or an indicator that a camera position violates a spatial constraint. In some embodiments, the LLM 144 may be configured to interact with one or more external computational modules through tool access mediated by the processor 104. As a non-limiting example, the processor 104 may accept an LLM request for visibility results and return computed visibility metrics for a simulated camera view 120. In some embodiments, tool-mediated interactions may include a field-of-view analysis module, a camera-state query module, a constraint-check module, and a render-summary module. As a non-limiting example, the render-summary module may compute which anatomical structures 116 appear in a simulated camera view 120 and provide the result to the LLM 144 for revising the proposed camera configuration 152.

With continued reference to FIG. 1, in some embodiments, generating the one or more LLM outputs 148 may include generating the one or more LLM outputs 148 as a function of the user instruction 136 and the spatial data 128. In some embodiments, spatial data 128 may be provided to the LLM 144 in a structured textual representation that preserves spatial relationships while reducing the amount of raw imaging information provided to the LLM 144. In some embodiments, generating the proposed camera configuration 152 may include selecting an initial camera position and orientation based on target anatomy and viewing objectives. As a non-limiting example, if the user instruction 136 requests an interior view of a cavity, the processor 104 may use spatial data 128 to identify an interior point of the cavity and use an orientation aligned with a principal axis of the cavity. In some embodiments, the apparatus 100 may include a camera configuration predictor model configured to propose initial camera configurations prior to LLM 144 generation. For the purposes of this disclosure, "camera configuration predictor model" is a machine learning model configured to generate camera configuration parameters from spatial data and a target anatomical label. In some embodiments, the camera configuration predictor model may be trained using training data comprising historical camera configuration sequences labeled by successful visualization outcomes. As a non-limiting example, training data may include logs from visualization sessions where a user navigated to target anatomical features and accepted views, enabling supervised learning of camera placement. In some embodiments, generating the proposed camera configuration 152 may include determining values for a zoom parameter and a field-of-view parameter based on a desired framing objective. As a non-limiting example, the LLM 144 may propose a wide field-of-view parameter to capture multiple connected structures, and the processor 104 may later narrow the field-of-view parameter during iterative revisions to satisfy visibility criteria for a specific target feature. In some embodiments, the apparatus 100 may store previously accepted proposed camera configurations 152 and use stored configurations as historical data for determining a visualization objective 156. As a non-limiting example, if prior navigation steps positioned a camera within a given anatomical structure 116, the apparatus 100 may use the prior configuration to constrain a new configuration or to generate a revised user instruction 164 reflecting the prior context.

With continued reference to FIG. 1, the processor 104 is configured to simulate a camera view 120 as a function of the proposed camera configuration 152 and the imaging data 112. For the purposes of this disclosure, "camera view" is a rendered or computed visualization corresponding to a camera configuration. In some cases, simulating the camera view 120 may include computing a two-dimensional projection from a three-dimensional coordinate space associated with the imaging data 112. In some embodiments, simulating the camera view 120 may comprise rendering the proposed camera configuration 152 within a three-dimensional coordinate space defined by the imaging data 112. For the purposes of this disclosure, "three-dimensional coordinate space" is a reference frame in which spatial positions are represented using three independent spatial dimensions. In some embodiments, the three-dimensional coordinate space may be defined directly by the imaging data 112. In such embodiments, the imaging data 112 may include voxel-based coordinates, surface mesh coordinates, point cloud coordinates, or combinations thereof, each expressed within a common spatial reference frame. The processor 104 may map imaging data 112 into the three-dimensional coordinate space such that each voxel, vertex, or point corresponds to a defined location relative to other anatomical structures 116. In some embodiments, the three-dimensional coordinate space may include an origin, one or more axes, and one or more scaling factors derived from imaging acquisition parameters associated with the imaging data 112. In such embodiments, spatial distances, orientations, and angles computed within the three-dimensional coordinate space correspond to physical or anatomical dimensions represented by the imaging data 112. In some embodiments, simulating the camera view 120 may comprise rendering the proposed camera configuration 152 within the three-dimensional coordinate space defined by the imaging data 112. In such embodiments, the processor 104 may position a virtual camera at a location specified by a camera position vector within the three-dimensional coordinate space and orient the virtual camera according to a camera orientation vector. The processor 104 may generate the camera view 120 by projecting elements of the imaging data 112 from the three-dimensional coordinate space into a two-dimensional image plane associated with the camera view 120. In some embodiments, the three-dimensional coordinate space may be used to enforce spatial constraints during simulation. In such embodiments, the processor 104 may determine whether a proposed camera configuration 152 corresponds to a physically realizable camera position by evaluating whether the camera position lies within permitted regions of the three-dimensional coordinate space and does not intersect restricted regions associated with anatomical structures 116. In some embodiments, the proposed camera configuration 152 may include at least one of a camera position vector, a camera orientation vector, a zoom parameter, and a field-of-view parameter. In some embodiments, rendering may include volumetric rendering operations, surface rendering operations, or hybrid operations combining volumetric and surface rendering. As a non-limiting example, volumetric rendering may include ray casting through voxel intensities, and surface rendering may include rasterization of a surface derived from segmented regions. In some embodiments, simulating the camera view 120 may include rendering volumetric imaging data (imaging data 112) through a camera model configured by the proposed camera configuration 152. As a non-limiting example, the camera model may include a perspective projection model with a specified field-of-view parameter and near and far clip planes. In some embodiments, simulating the camera view 120 may include rendering one or more segmented regions as overlays on a volumetric rendering. As a non-limiting example, boundary regions of an anatomical structure 116 may be displayed as contours or semi-transparent overlays to enable visibility evaluation of boundary regions. In some embodiments, the apparatus 100 may render at multiple resolutions during iterative revisions. As a non-limiting example, a low-resolution render may be used during early iterations for fast evaluation and a high-resolution render may be used only when a camera view 120 is near satisfying visualization criteria 124. In some embodiments, the rendering pipeline may compute auxiliary outputs used for evaluation, including a depth buffer, a normal buffer, a segmentation overlay map, and a boundary mask. As a non-limiting example, the depth buffer may be used to determine occlusion of boundary regions during visibility analysis. In some embodiments, when the apparatus 100 cannot generate a camera view 120 that satisfies visualization criteria 124 within a threshold number of iterations, the apparatus 100 may generate a revised user instruction 164 requesting additional constraints. As a non-limiting example, the revised user instruction 164 may request that the user select a target anatomical structure from a list of candidates.

With continued reference to FIG. 1, in some embodiments, simulating the camera view 120 may include constructing a virtual camera model parameterized by the proposed camera configuration 152 and applying the virtual camera model to the imaging data 112. In some embodiments, the virtual camera model may be defined within a three-dimensional coordinate system associated with spatial data 128, such that the camera position vector defines a camera origin and the camera orientation vector defines a viewing direction and rotational alignment relative to the spatial data 128. In some embodiments, the processor 104 may transform the imaging data 112 into a camera-centric coordinate frame prior to rendering, enabling consistent projection calculations across revised camera configurations 160.

With continued reference to FIG. 1, in some embodiments, simulating the camera view 120 may include computing a projection matrix as a function of the field-of-view parameter, zoom parameter, and a depth range associated with the imaging data 112. In some embodiments, the processor 104 may compute the projection matrix using a perspective projection formulation such that objects closer to the camera position vector appear larger within the camera view 120. In some embodiments, the processor 104 may alternatively compute an orthographic projection matrix when a visualization objective 156 specifies distortion-minimized inspection of an anatomical structure 116. In some embodiments, selection between perspective and orthographic projection models may be controlled by the visualization criteria 124.

With continued reference to FIG. 1, in some embodiments, simulating the camera view 120 may include sampling volumetric imaging data 112 along viewing rays emitted from the camera position vector through a virtual image plane defined by the field-of-view parameter. In some embodiments, the processor 104 may perform ray traversal through voxel-based imaging data 112 and accumulate intensity values, opacity values, or classification labels to generate pixel values for the camera view 120. In some embodiments, the processor 104 may apply transfer functions mapping voxel intensity ranges to color and opacity values to enhance contrast between anatomical structures 116.

With continued reference to FIG. 1, in some embodiments, simulating the camera view 120 may include rendering surface representations derived from segmented regions associated with one or more anatomical structures 116. In some embodiments, the processor 104 may generate polygonal meshes from segmented regions using surface extraction techniques, including but not limited to marching cubes or isosurface generation. In some embodiments, the processor 104 may rasterize the polygonal meshes using a graphics pipeline configured by the proposed camera configuration 152 to generate a surface-rendered camera view 120.

With continued reference to FIG. 1, in some embodiments, simulating the camera view 120 may include combining volumetric rendering and surface rendering within a single rendering pass or across multiple composited passes. In some embodiments, volumetric data may be rendered as a semi-transparent background, while surface representations of anatomical structures 116 may be rendered as opaque or semi-transparent overlays. In some embodiments, the processor 104 may apply depth testing and blending operations to ensure that surface overlays respect depth relationships encoded in the volumetric imaging data 112.

With continued reference to FIG. 1, in some embodiments, simulating the camera view 120 may include generating intermediate rendering artifacts used for downstream evaluation of visualization criteria 124. In some embodiments, the processor 104 may compute a depth buffer encoding distances from the camera position vector to rendered surfaces or volumetric intersections. In some embodiments, the processor 104 may compute a segmentation mask identifying pixel-level correspondence between rendered pixels and segmented regions of anatomical structures 116. In some embodiments, the processor 104 may compute boundary masks identifying pixels corresponding to boundary regions of anatomical structures 116 for use in visibility analysis.

With continued reference to FIG. 1, in some embodiments, simulating the camera view 120 may include evaluating occlusion relationships among anatomical structures 116 using the depth buffer and segmentation overlays. In some embodiments, the processor 104 may determine whether boundary regions of a target anatomical structure 116 are occluded by other anatomical structures 116 or imaging artifacts. In some embodiments, the processor 104 may generate occlusion metrics quantifying a proportion of boundary regions visible within the camera view 120, which may be compared against visualization criteria 124.

With continued reference to FIG. 1, in some embodiments, simulating the camera view 120 may include iterative refinement of rendering fidelity during generation of revised camera configurations 160. In some embodiments, the processor 104 may generate low-resolution camera views 120 during early iterations to reduce computational load while evaluating gross visibility constraints. In some embodiments, the processor 104 may increase rendering resolution, sampling density, or shading complexity when a revised camera view 172 approaches satisfaction of the visualization criteria 124.

With continued reference to FIG. 1, in some embodiments, simulating the camera view 120 may include enforcing physical feasibility constraints associated with the imaging data 112. In some embodiments, the processor 104 may restrict camera position vectors to locations that do not intersect segmented regions corresponding to solid anatomical structures 116. In some embodiments, the processor 104 may detect collisions between the camera position vector and spatial boundaries derived from the imaging data 112 and adjust the proposed camera configuration 152 accordingly prior to rendering.

With continued reference to FIG. 1, in some embodiments, when the processor 104 determines that no simulated camera view 120 satisfies the visualization criteria 124 within a predetermined iteration budget, the processor 104 may generate a revised user instruction 164 requesting additional constraints. In some embodiments, the revised user instruction 164 may prompt the user to specify a target anatomical structure 116, a preferred viewing angle, or a desired level of magnification. In some embodiments, the revised user instruction 164 may be generated as part of the one or more LLM outputs 148 and presented through the user interface 132 prior to continuing camera view simulation.

With continued reference to FIG. 1, the processor 104 is configured to determine whether the simulated camera view 120 satisfies one or more visualization criteria 124 associated with the user instruction 136. For the purposes of this disclosure, "visualization criteria" are constraints or requirements defining acceptable visualization outcomes. As a non-limiting example, visualization criteria 124 may include requirements regarding visibility of a target anatomical feature, viewpoint framing, or feasibility of a viewpoint within a three-dimensional structure represented by the imaging data 112. As further non-limiting examples, visualization criteria 124 may include physical or geometric constraints derived from the imaging data 112, including whether a camera position corresponding to the camera view 120 lies within a physically realizable region of the three-dimensional structure, whether the camera view 120 violates surface boundaries defined by segmented regions, or whether a line of sight associated with the camera view 120 intersects restricted or invalid regions of the imaging data 112.

With continued reference to FIG. 1, in some cases, determining whether the simulated camera view 120 satisfies the one or more visualization criteria 124 may include providing the simulated camera view 120 to the LLM 144 and generating, using the LLM 144, an evaluation output indicating whether the simulated camera view 120 satisfies the one or more visualization criteria 124. For the purposes of this disclosure, "evaluation output" is an output generated by an LLM that indicates whether a simulated camera view satisfies defined visualization criteria. In some cases, evaluation output may include a binary classification, a categorical label, a probability score, a confidence value, a ranked explanation, or a combination thereof. As a non-limiting example, the evaluation output may include a Boolean flag indicating satisfaction or non-satisfaction of visualization criteria 124. As a non-limiting example, the evaluation output may include a confidence score between zero and one representing likelihood of compliance. As a non-limiting example, the evaluation output may include an explanatory textual statement identifying which criteria were met or violated.

With continued reference to FIG. 1, in some embodiments, providing the simulated camera view 120 to the LLM 144 may include supplying a structured representation of the simulated camera view 120 rather than raw pixel data. As a non-limiting example, the structured representation may include camera parameters, depth maps, segmentation overlays, boundary coverage metrics, occlusion statistics, and identifiers of anatomical features referenced in the user instruction. In some embodiments, the processor may serialize such information into a prompt format that conditions the LLM 144 to perform evaluative reasoning over spatial constraints. In some embodiments, the LLM 144 may be configured with an evaluation prompt template that instructs the LLM 144 to compare attributes of the simulated camera view 120 against the visualization criteria 124 derived from the user instruction. As a non-limiting example, the prompt may include the anatomical feature requested, geometric coverage metrics indicating percentage of boundary region visible, occlusion indicators, and camera pose metadata. The LLM 144 may then apply transformer-based attention mechanisms to reason over the combined textual and structured inputs to determine compliance with the visualization criteria 124. In some embodiments, the evaluation output generated by the LLM 144 may include granular reasoning elements. As a non-limiting example, the evaluation output may identify that a target anatomical feature is partially occluded, that less than a threshold percentage of its boundary region is visible, or that the simulated camera view 120 violates a spatial feasibility constraint. In some embodiments, the processor may parse the evaluation output to extract structured compliance indicators, which may then be used to trigger generation of a revised camera configuration if the visualization criteria 124 are not satisfied. In some embodiments, the LLM 144 may be fine-tuned specifically for visualization compliance evaluation using training data comprising simulated camera views paired with labeled compliance outcomes. As a non-limiting example, training data may include rendered images of anatomical structures with associated annotations indicating whether boundary visibility thresholds are satisfied, whether occlusion exceeds an acceptable limit, or whether camera placement is physically realizable. In some embodiments, the LLM 144 may learn to associate structured spatial metrics with textual descriptions of adequacy, thereby enabling it to generate evaluation output consistent with predefined visualization criteria 124. In some embodiments, the processor 104 may combine the evaluation output of the LLM 144 with algorithmic geometric checks to produce a composite compliance determination. As a non-limiting example, the LLM 144 may generate an explanatory assessment while a geometric module verifies quantitative thresholds, and the processor 104 may reconcile both results before determining whether the simulated camera view 120 satisfies the one or more visualization criteria 124.

With continued reference to FIG. 1, in some embodiments, visualization criteria 124 may be generated or derived by the processor 104 as a function of one or more inputs associated with the user instruction 136, the imaging data 112, and the one or more LLM outputs 148. Visualization criteria 124 may be defined prior to simulation of a camera view 120, dynamically during simulation, or iteratively updated as revised camera configurations 160 are generated. In some embodiments, visualization criteria 124 may be explicitly derived from the user instruction 136. In such embodiments, the processor 104 may analyze semantic content of the user instruction 136 using the LLM 144 to extract one or more constraints related to a desired viewpoint, target anatomical structure 116, orientation, magnification, or region of interest. As a non-limiting example, a user instruction 136 specifying "show a cross-sectional view of the left ventricle" may result in visualization criteria 124 requiring that a segmented region corresponding to the left ventricle is present within a field of view of the camera view 120 and oriented relative to a known anatomical axis. In some embodiments, visualization criteria 124 may be generated as a function of spatial data 128 derived from the imaging data 112. In such embodiments, the processor 104 may generate geometric, topological, or visibility-based constraints based on segmented regions, boundary surfaces, or spatial relationships among anatomical structures 116. As a non-limiting example, visualization criteria 124 may include a requirement that a camera position corresponding to a camera view 120 does not intersect a segmented anatomical region, does not violate surface boundaries of a three-dimensional structure, or maintains an unobstructed line of sight to a target anatomical structure 116. In some embodiments, visualization criteria 124 may be derived from historical data associated with prior visualization configurations. In such embodiments, the processor 104 may access stored camera configurations, user interactions, or previously accepted camera views 120 associated with similar user instructions 136. The processor 104 may generate visualization criteria 124 that reflect common or preferred viewpoints previously used to visualize comparable anatomical structures 116. As a non-limiting example, historical data may indicate that a particular oblique angle is routinely used to inspect a given anatomical structure, and visualization criteria 124 may require that simulated camera views 120 fall within an angular tolerance of that angle. In some embodiments, visualization criteria 124 may be derived from predefined system constraints or rule sets stored in memory 108. Such constraints may include rendering constraints, anatomical plausibility constraints, safety constraints, or physical realizability constraints. As a non-limiting example, visualization criteria 124 may require that a camera view 120 corresponds to a camera position that is physically realizable within a three-dimensional structure represented by the imaging data 112, or that a camera orientation avoids excessive distortion, clipping, or occlusion. In some embodiments, visualization criteria 124 may be dynamically updated during iterative generation of revised camera configurations 160. In such embodiments, the processor 104 may evaluate intermediate simulated camera views 120 and refine visualization criteria 124 based on detected deficiencies. As a non-limiting example, if a simulated camera view 120 fails to sufficiently expose a boundary region of an anatomical structure 116, the processor 104 may update visualization criteria 124 to emphasize boundary visibility in subsequent simulation iterations. In some embodiments, visualization criteria 124 may be generated as a weighted combination of multiple criteria sources, including user-derived constraints, spatial constraints, historical preferences, and system-defined feasibility constraints. The processor 104 may evaluate simulated camera views 120 against the visualization criteria 124 using threshold-based logic, scoring functions, or confidence metrics to determine whether a simulated camera view 120 satisfies the visualization criteria 124. In some embodiments, when segmentation confidence is low for a target anatomical structure 116, the apparatus 100 may adjust visualization criteria 124 to require reduced reliance on boundary visibility and may request user confirmation. As a non-limiting example, the apparatus 100 may display an uncertainty indicator and propose alternative camera views 120 that maximize visibility under uncertain segmentation.

With continued reference to FIG. 1, in some embodiments, determining whether the simulated camera view 120 satisfies the one or more visualization criteria 124 may include identifying at least one anatomical feature from the user instruction 136 and analyzing visibility of one or more boundary regions of the at least one anatomical feature within the simulated camera view 120, wherein the one or more visualization criteria 124 may include a requirement that the at least one anatomical feature associated with the user instruction 136 is present within a field of view of the simulated camera view 120. For the purposes of this disclosure, "anatomical feature" is a semantic element extracted from a user instruction that corresponds to an anatomical structure or a portion. An anatomical feature may include a keyword, phrase, or concept identifying a target of visualization rather than a physical structure itself. For the purposes of this disclosure, "boundary region" is a spatial region associated with an anatomical structure that defines an interface between the anatomical structure and surrounding spatial regions. A boundary region may include a demarcation used to evaluate exposure, occlusion, or extent of an anatomical structure 116. For the purposes of this disclosure, "visibility" is a determination indicating whether a boundary region or an anatomical structure mapped from an anatomical feature is perceptible within a camera view under a given camera configuration. For the purposes of this disclosure, "field of view" is a spatial extent of a scene rendered by a camera configuration and projected into a camera view. The field of view defines a subset of a three-dimensional coordinate space that is visible within the camera view 120.

With continued reference to FIG. 1, in some embodiments, the processor 104 may extract or identify at least one anatomical feature from the user instruction 136 by performing natural-language processing on the user instruction 136 to detect one or more anatomical tokens. In such embodiments, the processor 104 may segment the user instruction 136 into tokens, normalize the tokens into canonical forms, and identify candidate anatomical phrases using a domain vocabulary stored in memory 108. In some embodiments, identifying at least one anatomical feature from the user instruction 136 may include executing a concept mapping model configured to map free-form instruction language to one or more anatomical labels represented in spatial data 128. For the purposes of this disclosure, "concept mapping model" is a machine learning model configured to map natural language tokens to a controlled vocabulary of domain concepts. In some embodiments, the concept mapping model may be trained using training data comprising pairs of text phrases and canonical anatomical labels. As a non-limiting example, the training data may include clinician-authored phrases extracted from procedure reports, clinical notes, medical device instructions, anatomy textbooks, and annotation guidelines, wherein each phrase is labeled with a canonical anatomical term. In some embodiments, the concept mapping model may incorporate an anatomical ontology as a reference structure, and the apparatus 100 may use ontology relationships to interpret ambiguous or incomplete instructions. As a non-limiting example, if a user instruction references a structure family rather than a specific structure, the concept mapping model may output candidate anatomical labels within that family for subsequent evaluation by visualization criteria 124.

With continued reference to FIG. 1, in some embodiments, analyzing visibility of one or more boundary regions may include mapping an anatomical feature identified from the user instruction 136 to one or more anatomical structures 116 represented in spatial data 128 and identifying boundary regions associated with the mapped anatomical structures 116. In such embodiments, the processor 104 may evaluate whether the boundary regions are projected into the field of view of the simulated camera view 120. In some embodiments, determining visibility may include computing whether projected boundary regions are occluded by intervening anatomical structures 116 or other spatial elements represented in the imaging data 112. In such embodiments, the processor 104 may use depth information, surface normals, or segmentation masks generated during rendering of the camera view 120 to determine whether the boundary regions are perceptible. In some embodiments, determining whether an anatomical feature is present within the field of view may include evaluating whether projected coordinates corresponding to the boundary regions associated with the anatomical feature intersect a defined image boundary associated with the camera view 120. The processor 104 may require that a minimum portion of the boundary region or a minimum number of boundary points appear within the field of view to satisfy the visualization criteria 124. In some embodiments, visibility determinations may be expressed as one or more quantitative measures, including a proportion of boundary regions visible within the field of view, a spatial distribution of visible regions, or a confidence score indicating adequacy of visualization. The processor 104 may compare such measures against thresholds defined by the visualization criteria 124 to determine whether the simulated camera view 120 satisfies the one or more visualization criteria 124.

With continued reference to FIG. 1, in some embodiments, analyzing visibility of one or more boundary regions may include mapping an anatomical feature identified from the user instruction 136 to one or more anatomical structures 116 represented in spatial data 128 and identifying boundary regions associated with the mapped anatomical structures 116. In such embodiments, the processor 104 may evaluate whether the boundary regions are projected into the field of view of the simulated camera view 120. In some embodiments, determining visibility may include computing whether projected boundary regions are occluded by intervening anatomical structures 116 or other spatial elements represented in the imaging data 112. In such embodiments, the processor 104 may use depth information, surface normals, or segmentation masks generated during rendering of the camera view 120 to determine whether the boundary regions are perceptible. In some embodiments, determining whether an anatomical feature is present within the field of view may include evaluating whether projected coordinates corresponding to the boundary regions associated with the anatomical feature intersect a defined image boundary associated with the camera view 120. The processor 104 may require that a minimum portion of the boundary region or a minimum number of boundary points appear within the field of view to satisfy the visualization criteria 124. In some embodiments, visibility determinations may be expressed as one or more quantitative measures, including a proportion of boundary regions visible within the field of view, a spatial distribution of visible regions, or a confidence score indicating adequacy of visualization. The processor 104 may compare such measures against thresholds defined by the visualization criteria 124 to determine whether the simulated camera view 120 satisfies the one or more visualization criteria 124.

With continued reference to FIG. 1, in some embodiments, projecting boundary regions into the field of view may include transforming three-dimensional coordinates of boundary region elements from the three-dimensional coordinate space into a two-dimensional image plane using a projection transform derived from the proposed camera configuration 152. In such embodiments, the processor 104 may apply a view matrix corresponding to the camera position vector and camera orientation vector, followed by a projection matrix corresponding to the field-of-view parameter and zoom parameter, to generate image-space coordinates for boundary region elements. In some embodiments, determining whether boundary regions are occluded may include comparing depth values associated with projected boundary region elements against depth values of other rendered elements along corresponding viewing rays. In such embodiments, the processor 104 may determine occlusion by evaluating whether depth values of intervening voxels, surfaces, or segmented regions are closer to the camera position than depth values of the boundary region elements. Boundary region elements for which nearer depth values are detected may be classified as occluded. In some embodiments, the processor 104 may evaluate orientation-dependent visibility of boundary regions using surface normal information. In such embodiments, the processor 104 may compute an angle between a surface normal vector associated with a boundary region and a viewing direction associated with the simulated camera view 120. Boundary regions whose surface normals are oriented away from the camera beyond an angular threshold may be weighted lower or excluded when computing visibility metrics. In some embodiments, analyzing visibility may include generating a visibility mask or boundary visibility map indicating which portions of the boundary regions are visible within the camera view 120. In such embodiments, the visibility mask may be generated by combining projection results, depth comparisons, and segmentation masks into a composite representation. The processor 104 may use the visibility mask to compute quantitative measures, including contiguous visible boundary length, visible surface area, or spatial dispersion of visible boundary regions. In some embodiments, determining whether the anatomical feature is present within the field of view may include evaluating not only inclusion within image boundaries but also spatial placement within the field of view. In such embodiments, the processor 104 may determine whether visible boundary regions are located within a central portion of the camera view 120, within a predefined region of interest, or within a tolerance distance from a desired focal location derived from the visualization criteria 124. In some embodiments, the processor 104 may aggregate multiple visibility metrics into a composite visibility score. In such embodiments, the composite visibility score may be generated as a weighted combination of visible boundary proportion, occlusion ratio, angular orientation score, and spatial coverage score. The processor 104 may compare the composite visibility score against one or more thresholds defined by the visualization criteria 124 to determine whether the simulated camera view 120 satisfies the visualization criteria 124 or whether a revised camera configuration 160 should be generated. In some embodiments, intermediate visibility analysis outputs, including visibility masks, depth comparison results, and composite scores, may be stored in memory 108 and used to guide subsequent generation of revised camera configurations 160. In such embodiments, specific failure modes identified during visibility analysis may be mapped to corresponding camera parameter adjustments, including translation of the camera position vector, rotation of the camera orientation vector, or modification of the field-of-view parameter.

With continued reference to FIG. 1, in some embodiments, determining whether the simulated camera view 120 satisfies the one or more visualization criteria 124 may include determining whether the simulated camera view 120 corresponds to a physically realizable camera position within a three-dimensional structure represented by the imaging data 112 as a function of a spatial constraint associated with the three-dimensional structure. For the purposes of this disclosure, "physically realizable camera position" is a camera position within a three-dimensional coordinate space that does not violate spatial constraints imposed by imaging data representing a three-dimensional structure. A physically realizable camera position may correspond to a location from which a camera view 120 can be generated without intersecting restricted regions of the three-dimensional structure. For the purposes of this disclosure, "spatial constraint" is a rule or condition defining permissible spatial locations or orientations within a three-dimensional coordinate space associated with imaging data. A spatial constraint may restrict camera placement or viewing geometry relative to anatomical structures 116 represented in the imaging data 112. In some embodiments, a spatial constraint may be derived from segmented regions, boundary representations, or surface representations, and may define permitted regions for a camera position and prohibited regions where a camera would intersect an anatomical boundary. As a non-limiting example, a spatial constraint may define a navigable cavity volume and prohibit camera positions outside the cavity volume. In some embodiments, determining whether the simulated camera view 120 corresponds to a physically realizable camera position within a three-dimensional structure may include performing collision detection between a camera position and anatomical boundaries represented by spatial data 128. As a non-limiting example, collision detection may include evaluating whether a camera position lies within a permitted cavity volume defined by segmented regions. In some embodiments, physical realizability evaluation may include constraints associated with an imaging device 176 geometry, including device length, articulation constraints, or allowable curvature. As a non-limiting example, if an imaging device 176 is catheter-based, a constraint may require that a path to a camera position be reachable under curvature limits.

With continued reference to FIG. 1, in some embodiments, the apparatus 100 may implement a reachability model configured to determine whether a camera position is reachable by an imaging device 176 under device constraints. For the purposes of this disclosure, "reachability model" is a computational model configured to determine reachability of a target pose given device constraints. In some embodiments, the reachability model may be trained using training data comprising device motion logs and successful pose outcomes. As a non-limiting example, training data may include recorded device trajectories from clinical procedures, simulated device trajectories generated under physics-based constraints, and labeled outcomes indicating which target poses were reachable.

With continued reference to FIG. 1, in some embodiments, determining whether the simulated camera view 120 satisfies visualization criteria 124 may include computing one or more quantitative metrics describing visibility of target anatomy. As a non-limiting example, a visibility metric may be computed as a fraction of boundary pixels of a target anatomical feature that are visible and unoccluded. In some embodiments, determining whether the simulated camera view 120 satisfies visualization criteria 124 may include evaluating a framing criterion that the target anatomical feature occupies a defined portion of the simulated camera view 120. As a non-limiting example, a framing metric may include a normalized area of the target feature in the simulated camera view 120 or a minimum pixel coverage threshold. In n some embodiments, the apparatus 100 may implement a visibility scoring model configured to predict whether a camera view 120 will satisfy visualization criteria 124 without fully rendering the view. For the purposes of this disclosure, "visibility scoring model" is a machine learning model configured to estimate a visibility outcome for a camera configuration based on spatial data and camera parameters. In some embodiments, the visibility scoring model may be trained using training data comprising camera configurations paired with computed or labeled visibility outcomes. As a non-limiting example, the training data may include synthetic samples generated by randomly sampling camera position and orientation vectors within anatomical volumes and rendering views to compute ground-truth visibility metrics for target features. In some embodiments, the visibility scoring model may be trained using real user interaction sessions where accepted camera views and rejected camera views are logged. As a non-limiting example, accepted camera views may be treated as positive labels and rejected camera views as negative labels, enabling training of a classifier predicting satisfaction of visualization criteria 124.

With continued reference to FIG. 1, in response to determining that the simulated camera view 120 does not satisfy the one or more visualization criteria 124 (e.g., evaluation output), the processor 104 is configured to generate, using the LLM 144, one or more revised camera configurations 160. For the purposes of this disclosure, "revised camera configuration" is a camera configuration generated to modify a previously generated camera configuration. As a non-limiting example, a revised camera configuration 160 may include an adjusted camera position vector, an adjusted camera orientation vector, an adjusted zoom parameter, an adjusted field-of-view parameter, or any combination thereof relative to a previously proposed camera configuration 152.

With continued reference to FIG. 1, in some embodiments, generating the one or more revised camera configurations 160 may include identifying one or more parameters of the proposed camera configuration 152 that caused failure of the visualization criteria 124. In such embodiments, the processor 104 may analyze evaluation outputs generated during simulation of the camera view 120, including visibility metrics, occlusion metrics, boundary exposure metrics, or physical feasibility indicators. The processor 104 may determine which parameters of the proposed camera configuration 152 contributed to a failure condition and selectively modify those parameters while maintaining other parameters unchanged.

With continued reference to FIG. 1, in some embodiments, the processor 104 may provide feedback data to the LLM 144 describing one or more failed visualization criteria 124. The feedback data may include structured or semi-structured representations of failed constraints, spatial relationships between anatomical structures 116, and deficiencies in the simulated camera view 120. The LLM 144 may use the feedback data to generate revised camera configurations 160 that are biased toward satisfying the failed visualization criteria 124 while preserving semantic intent of the user instruction 136.

With continued reference to FIG. 1, in some embodiments, generating the revised camera configuration 160 may include performing a constrained search over a camera configuration parameter space. In such embodiments, the LLM 144 may propose candidate adjustments to one or more camera parameters within predefined bounds derived from spatial data 128 or system constraints stored in memory 108. The processor 104 may evaluate candidate revised camera configurations 160 iteratively until one or more revised camera views 172 satisfy the visualization criteria 124 or until a termination condition is reached.

With continued reference to FIG. 1, in some embodiments, the LLM 144 may generate revised camera configurations 160 using prompt conditioning that incorporates prior camera configurations, failed visualization criteria 124, and historical visualization data. The prompt conditioning may guide the LLM 144 to generate revised camera configurations 160 that reflect learned anatomical conventions, common diagnostic viewpoints, or previously accepted visualization patterns associated with similar anatomical structures 116.

With continued reference to FIG. 1, in some embodiments, the processor 104 may generate revised camera configurations 160 using a hybrid approach combining LLM-generated proposals with algorithmic refinement. In such embodiments, the LLM 144 may generate a high-level adjustment directive, such as increasing exposure of a boundary region or re-centering a target anatomical structure 116, and the processor 104 may translate the directive into quantitative parameter adjustments applied to the camera position vector, camera orientation vector, zoom parameter, or field-of-view parameter.

With continued reference to FIG. 1, in some embodiments, the processor 104 may enforce physical or geometric constraints when generating revised camera configurations 160. In such embodiments, revised camera configurations 160 that violate spatial constraints, intersect segmented regions associated with anatomical structures 116, or result in non-physically realizable viewpoints may be discarded prior to simulation. This enforcement may occur before or after invocation of the LLM 144.

With continued reference to FIG. 1, in some embodiments, the apparatus 100 may maintain an audit trail of proposed camera configurations 152 and revised camera configurations 160 for quality review. As a non-limiting example, the apparatus 100 may store a record of iteration identifiers, parameter changes, failed visualization criteria 124, and resulting revised camera configurations 160. The audit trail may be used for debugging, regulatory review, model improvement, or retraining of machine-learning components.

With continued reference to FIG. 1, in some embodiments, the apparatus 100 may include a rejection classifier model configured to predict whether a simulated camera view 120 should be rejected prior to display. For the purposes of this disclosure, "rejection classifier model" is a machine learning model configured to classify a camera view 120 as compliant or noncompliant with visualization criteria 124. In some embodiments, the rejection classifier model may be trained using training data comprising pairs of rendered camera views and labels indicating acceptance or rejection. As a non-limiting example, training data may include clinician-labeled examples where boundary visibility is insufficient, target anatomy is absent from a field of view, occlusion exceeds a threshold, or a camera pose is physically unrealizable.

With continued reference to FIG. 1, in some embodiments, outputs of the rejection classifier model may be used to gate simulation output prior to user display. In such embodiments, simulated camera views 120 predicted to be noncompliant may be suppressed and used solely to inform generation of revised camera configurations 160. This configuration prevents presentation of noncompliant camera views 120 while enabling iterative improvement of camera configurations through feedback-driven refinement.

With continued reference to FIG. 1, the processor 104 is configured to simulate corresponding revised camera view 172 instances as a function of the one or more revised camera configurations 160. For the purposes of this disclosure, "revised camera view" is a camera view corresponding to a revised camera configuration. As a non-limiting example, the processor 104 simulates a sequence of revised camera views 172 generated from successive revised camera configurations 160.

With continued reference to FIG. 1, in some embodiments, generating one or more revised camera configurations 160 may include iteratively generating the one or more revised camera configurations 160 until at least one revised camera view 172 satisfies the one or more visualization criteria 124, wherein one or more revised camera views 172 generated prior to satisfaction of the one or more visualization criteria 124 may be not output through the user interface 132. In some embodiments, the processor 104 may store non-output revised camera views 172 as internal simulation results in the memory 108, and may store metadata describing reasons for noncompliance with visualization criteria 124. As a non-limiting example, metadata may include an indicator that a target anatomical feature is not visible, an indicator that an anatomical boundary is occluded, or an indicator that a spatial constraint is violated.

With continued reference to FIG. 1, in some embodiments, generating one or more revised camera configurations 160 may include iteratively adjusting at least one of camera position vector, camera orientation vector, zoom parameter, and field-of-view parameter until visualization criteria 124 are satisfied. As a non-limiting example, the processor 104 may adjust a camera position along a gradient direction computed from signed distance fields to move away from boundary collisions while retaining visibility of a target anatomical feature.

With continued reference to FIG. 1, in some embodiments, revised camera configuration 160 generation may include a search process over candidate camera configurations guided by an objective function. For the purposes of this disclosure, "objective function" is a function mapping a candidate camera configuration to a scalar value representing compliance with visualization criteria. In some embodiments, the objective function may combine multiple criteria including visibility, framing, and constraint satisfaction into a single score. As a non-limiting example, the objective function may penalize occlusion of boundary regions, penalize violations of spatial constraints, and reward inclusion of specified anatomical features in the simulated camera view 120. In some embodiments, the processor 104 may provide objective function feedback to the LLM 144 to guide generation of revised camera configurations 160. As a non-limiting example, the processor 104 may provide a statement indicating that the target feature is partially occluded and that a revised camera orientation vector should be rotated to reduce occlusion.

With continued reference to FIG. 1, in some embodiments, the apparatus 100 may limit the number of iterations or enforce timing constraints. As a non-limiting example, the processor 104 may terminate an iterative loop after a maximum number of revised camera configurations 160 are generated and may output a best-scoring camera view 120 or may generate a revised user instruction 164 requesting clarification.

With continued reference to FIG. 1, in response to determining that the simulated camera view 120 satisfies the one or more visualization criteria 124 (e.g., evaluation output), the processor 104 is configured to output the camera view 120 corresponding to the proposed camera configuration 152. As a non-limiting example, outputting the camera view 120 may include modifying the user interface 132 to display the camera view 120 on the display device 140.

With continued reference to FIG. 1, in some embodiments, determining whether the simulated camera view 120 satisfies the one or more visualization criteria 124 (e.g., evaluation output) may include identifying at least one anatomical feature from the user instruction 136. In some embodiments, identifying the anatomical feature may include executing a natural-language extraction model configured to map a phrase to an anatomical label used within spatial data 128. As a non-limiting examples, outputting the camera view 120 may include updating a visualization position of the imaging data 112 within a three-dimensional rendering environment, adjusting a viewpoint of an interactive viewer, or replacing a previously displayed camera view 120 with the camera view 120 corresponding to the proposed camera configuration 152. In some embodiments, outputting the camera view 120 may include synchronizing the camera view 120 with auxiliary visual elements, including segmentation overlays, boundary contours, annotations, or measurement indicators associated with anatomical structures 116. As a non-limiting examples, outputting the camera view 120 may include transmitting rendering instructions to a graphics processing unit configured to render the camera view 120 in real time, caching the camera view 120 in memory 108 for subsequent retrieval, or exporting the camera view 120 as part of a report, snapshot, or visualization sequence associated with the user instruction 136. In some embodiments, the camera view 120 may be output as a static image, an interactive three-dimensional view, or a time-varying sequence generated by incremental camera motion. As a non-limiting examples, outputting the camera view 120 may include generating an instruction response 168 as part of the one or more LLM outputs 148, wherein the instruction response 168 provides a textual or visual explanation of the camera view 120, identifies anatomical structures 116 visible within the camera view 120, or describes how the camera view 120 satisfies the visualization criteria 124. In some embodiments, the processor 104 may modify the user interface 132 to present the instruction response 168 concurrently with the camera view 120. As a non-limiting examples, outputting the camera view 120 may include generating and transmitting a control signal as a function of the proposed camera configuration 152 to actuate an imaging device 176. In such embodiments, actuating the imaging device 176 may cause movement, reorientation, or reconfiguration of a physical imaging system to acquire additional imaging data 112 corresponding to the proposed camera configuration 152. As a non-limiting examples, outputting the camera view 120 may include storing the camera view 120 and associated camera configuration parameters in memory 108 as part of a visualization session history, enabling subsequent replay, comparison, or audit of camera views generated in response to the user instruction 136.

With continued reference to FIG. 1, in some embodiments, determining whether the simulated camera view 120 satisfies the one or more visualization criteria 124 may include analyzing visibility of one or more boundary regions of the at least one anatomical feature within the simulated camera view 120, wherein the one or more visualization criteria 124 may include a requirement that the at least one anatomical feature associated with the user instruction 136 is present within a field of view of the simulated camera view 120. As a non-limiting example, analyzing visibility may include projecting boundary points into a camera plane and computing occlusion using depth information generated during rendering.

With continued reference to FIG. 1, in some embodiments, outputting the camera view 120 may include modifying a visualization position of the imaging data 112 associated with the camera view 120. For the purposes of this disclosure, "visualization position" is a state defining a spatial relationship between imaging data 112 and a camera view 120 within a three-dimensional coordinate space. The visualization position may specify how imaging data 112 are spatially situated, oriented, and rendered relative to a camera configuration. In some embodiments, modifying the visualization position may include modifying a viewpoint origin, a navigation position within a cavity, a camera pose state, or a rendering transform used to generate the displayed camera view 120. In some embodiments, modifying the visualization position may include applying a transformation matrix to the imaging data 112 within the three-dimensional coordinate space. In such embodiments, the processor 104 may update translation, rotation, or scaling components of the transformation matrix such that the imaging data 112 are repositioned relative to the camera position vector and camera orientation vector associated with the camera configuration. In some embodiments, modifying the visualization position may include updating a navigation state associated with internal or external traversal of an anatomical structure 116. In such embodiments, the processor 104 may modify a navigation position to reflect movement along a predefined path, lumen, or cavity represented in the imaging data 112, thereby causing subsequent camera views 120 to be rendered from updated spatial locations within the anatomical structure 116.

With continued reference to FIG. 1, in some embodiments, outputting the camera view 120 may include modifying the user interface 132 to display the camera view 120 and the imaging data 112 in the modified visualization position. As a non-limiting example, the user interface 132 may display the camera view 120 in a primary viewport and display contextual imaging overlays indicating the navigation position relative to anatomical structures 116. In some embodiments, modifying the user interface 132 may include updating a primary viewport to display the camera view 120 and updating one or more auxiliary interface elements to reflect the visualization position. In such embodiments, the user interface 132 may display contextual indicators including orientation markers, navigation cues, depth indicators, or spatial overlays illustrating the position of the camera view 120 relative to anatomical structures 116 represented in the imaging data 112. In some embodiments, modifying the user interface 132 may include synchronizing user interaction controls with the modified visualization position. In such embodiments, user input received through the user interface 132 may be interpreted relative to the updated visualization position, enabling subsequent user instructions 136 to refine camera movement, adjust field-of-view parameters, or request additional visualization actions based on the currently displayed camera view 120.

With continued reference to FIG. 1, in some embodiments, outputting the camera view 120 may include generating an instruction response 168 as part of the one or more LLM outputs 148 as a function of the user instruction 136 and the simulated camera view 120, wherein the instruction response 168 may be generated after the simulated camera view 120 satisfies the one or more visualization criteria 124. For the purposes of this disclosure, "instruction response" is an output generated in response to a user instruction. As a non-limiting example, the instruction response 168 may include a textual description identifying a current anatomical structure being viewed and listing structures visible in the camera view 120. In some embodiments, generating the instruction response 168 may include generating a textual explanation of how the camera view 120 satisfies the visualization criteria 124. As a non-limiting example, the instruction response 168 may state that a named target anatomical feature is centered and that boundary regions are visible without occlusion. In some embodiments, generating the instruction response 168 may include referencing spatial data 128 to provide anatomical context, including a list of visible structures and their relationships. As a non-limiting example, the instruction response 168 may describe that a camera view 120 is inside a cavity and that connecting vessels are visible in specified directions. In some embodiments, the instruction response 168 may be generated by the LLM 144 using a context that includes the user instruction 136, a summary of the proposed camera configuration 152, and a summary of visible anatomy derived from evaluation results. As a non-limiting example, the processor 104 may compute a set of visible anatomical labels and provide those labels to the LLM 144 to generate a user-facing explanation.

With continued reference to FIG. 1, in some embodiments, outputting the camera view 120 may include modifying the user interface 132 to display the instruction response 168 concurrently with the camera view 120. As a non-limiting example, the user interface 132 may display the instruction response 168 in a chat pane adjacent to a visualization pane displaying the camera view 120. as a non-limiting example, the instruction response 168 may be displayed as an overlay within the camera view 120, wherein the overlay includes textual annotations describing visible anatomical structures 116 or explaining how the camera view 120 satisfies the visualization criteria 124. In such embodiments, the overlay may be spatially anchored to regions of the camera view 120 corresponding to anatomical structures 116. As a non-limiting example, the user interface 132 may display the instruction response 168 in a collapsible or expandable panel that updates dynamically as the camera view 120 is modified. In such embodiments, the instruction response 168 may reflect changes in the visualization position, camera orientation, or target anatomical feature without interrupting display of the camera view 120. As a non-limiting example, the instruction response 168 may be presented as a stepwise or structured explanation synchronized with user interaction. In such embodiments, the user interface 132 may highlight portions of the instruction response 168 as the user navigates within the camera view 120, enabling contextual guidance tied to the currently displayed anatomical region. As a non-limiting example, the instruction response 168 may be rendered using visual cues in addition to text, including icons, color-coded indicators, or emphasis markers identifying anatomical structures 116 referenced in the instruction response 168. In such embodiments, the visual cues may correspond to segmentation overlays or boundary regions visible within the camera view 120. As a non-limiting example, the instruction response 168 may be generated in multiple levels of detail and selectively displayed based on user interaction. In such embodiments, the user interface 132 may initially display a concise instruction response 168 and allow the user to request additional detail, wherein expanded instruction responses 168 are displayed concurrently with the camera view 120 without modifying the visualization position. As a non-limiting example, the instruction response 168 may be displayed using a modality different from the camera view 120, including an audio output synchronized with visual display. In such embodiments, the user interface 132 may present spoken instruction responses 168 while maintaining display of the camera view 120 on the display device 140. As a non-limiting example, the user interface 132 may log the instruction response 168 alongside the camera view 120 as part of a visualization session history. In such embodiments, previously displayed instruction responses 168 may remain accessible while the camera view 120 is updated or replaced in response to subsequent user instructions 136.

With continued reference to FIG. 1, in some embodiments, outputting the camera view 120 may include generating and transmitting a control signal 180 as a function of the proposed camera configuration 152 and actuating an imaging device 176 as a function of the control signal 180. For the purposes of this disclosure, "control signal" is a signal that encodes one or more commands for configuring, positioning, or actuating an imaging device. A control signal may represent an executable instruction derived from a proposed camera configuration 152. For the purposes of this disclosure, "imaging device" is a hardware system configured to acquire imaging data from a physical environment or subject. An imaging device 176 may include at least one imaging sensor and one or more controllable components affecting image acquisition. In some embodiments, actuating the imaging device 176 may include controlling an imaging sensor orientation, a physical camera pose, a lens setting, or a device navigation parameter associated with image acquisition. In some embodiments, generating the control signal 180 may include translating a camera position vector and a camera orientation vector of the proposed camera configuration 152 into actuator commands, and transmitting the actuator commands to the imaging device 176 through a wired or wireless interface. As a non-limiting example, the imaging device 176 may be an endoscopic imaging system with controllable pose, and the control signal 180 may actuate steering to align the physical viewpoint with the proposed camera configuration 152. In some embodiments, generating and transmitting the control signal 180 as a function of the proposed camera configuration 152 may include mapping a virtual camera position to a physical imaging device 176 pose command. As a non-limiting example, a mapping may include converting coordinate units from imaging-data coordinates into device actuator coordinates. In some embodiments, actuating the imaging device 176 may include controlling a mechanical articulation system, a steerable catheter, a gimbal system, or a robotic imaging platform. As a non-limiting example, an actuation command may include a sequence of actuator setpoints that move a physical camera to a target position and orientation. In some embodiments, the apparatus 100 may include a device feedback module that receives sensor feedback from the imaging device 176 and updates the proposed camera configuration 152 or revised camera configuration 160 based on measured device pose. As a non-limiting example, feedback may include an actual device pose measurement that is compared to a target pose derived from the proposed camera configuration 152, and deviations may trigger generation of a revised camera configuration 160.

With continued reference to FIG. 1, in some embodiments, training data for segmentation models, concept mapping models, visibility scoring models, reachability models, and rejection classifier models may be collected under data governance constraints. As a non-limiting example, training data may be de-identified, aggregated, or processed under privacy-preserving protocols prior to model training.

With continued reference to FIG. 1, in some embodiments, the apparatus 100 may maintain model version metadata and training dataset identifiers in the memory 108 to support reproducibility and validation. As a non-limiting example, the apparatus 100 may store a record of which segmentation model version generated spatial data 128 used for a given camera view 120.

With continued reference to FIG. 1, in some embodiments, processor 104 may be communicatively connected with database. For example, and without limitation, in some cases, database may be local to processor 104. In another example, and without limitation, database may be remote to processor 104 and communicative with processor 104 by way of one or more networks. The network may include, but is not limited to, a cloud network, a mesh network, and the like. By way of example, a "cloud-based" system can refer to a system which includes software and/or data which is stored, managed, and/or processed on a network of remote servers hosted in the "cloud," e.g., via the Internet, rather than on local severs or personal computers. A "mesh network" as used in this disclosure is a local network topology in which the infrastructure processor 104 connects directly, dynamically, and non-hierarchically to as many other computing devices as possible. A "network topology" as used in this disclosure is an arrangement of elements of a communication network.

With continued reference to FIG. 1, in some embodiments, database may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

With continued reference to FIG. 1, in some embodiments, each machine learning model described herein, including without limitation the large language model (LLM) 144, the concept mapping model, the segmentation model, the rejection classifier model, and any model configured to generate or revise camera configurations, may be trained using task-specific training data corresponding to the function performed by the respective model. In some embodiments, training data for the segmentation model may include annotated imaging datasets comprising CT, MRI, ultrasound, fluoroscopy, endoscopic, or other volumetric or planar imaging data with voxel-level, pixel-level, or region-level anatomical labels generated by clinicians, trained annotators, atlas-based labeling systems, or semi-automated annotation pipelines. In some embodiments, training data for the concept mapping model and the LLM 144 may include pairs of natural-language instructions and canonical anatomical labels, structured anatomical ontologies, clinical procedure reports, medical textbooks, imaging interpretation reports, device navigation logs, and curated corpora of domain-specific documentation. In some embodiments, training data for the rejection classifier model may include rendered camera views paired with acceptance or rejection labels, visibility scores, boundary coverage metrics, and clinician-provided assessments of visualization adequacy. In some embodiments, training data for models configured to generate or revise camera configurations may include pairs of user instructions, imaging data representations, and corresponding target camera parameters or navigation trajectories validated by domain experts. In some embodiments, such training data may be sourced from internal institutional imaging archives, public medical imaging repositories, structured hospital databases, licensed medical datasets, synthetic data generated through simulation of anatomical environments, and feedback collected during system deployment. In some embodiments, training may include supervised learning, semi-supervised learning, self-supervised learning, reinforcement learning, or fine-tuning of pretrained models using domain-specific corpora to adapt the models to anatomical visualization tasks described herein.

With continued reference to FIG. 1, in some embodiments, the apparatus 100 may be configured to address technical challenges associated with manual camera manipulation, inconsistent viewpoint selection across users, and inefficiencies in identifying optimal visualization of target anatomical structures 116 within complex three-dimensional imaging data 112. In some embodiments, the processor 104 may coordinate interaction between the user interface 132, the LLM 144, segmentation modules, rendering pipeline, and visualization criteria 124 evaluation engine to automatically translate a user instruction 136 into a proposed camera configuration 152, simulate a camera view 120, and iteratively refine the configuration until objective visualization requirements are satisfied. In some embodiments, the system may suppress intermediate LLM outputs 148 that fail to meet the visualization criteria 124, thereby reducing risk of presenting misleading or suboptimal viewpoints to a user.

With continued reference to FIG. 1, in some embodiments, the processor 104 may further integrate historical visualization data, prior user preferences, and structured spatial data 128 derived from segmentation of imaging data 112 to determine a visualization objective 156 when a user instruction 136 is incomplete or underspecified. In some embodiments, the apparatus 100 may maintain traceability of iterations between proposed camera configurations XXX and revised camera configurations 160 to support validation, auditing, and reproducibility. In some embodiments, the system may optionally generate an instruction response 168 explaining why a particular camera view 120 was selected or revised, thereby improving transparency and usability in clinical, research, or procedural contexts.

With continued reference to FIG. 1, the present disclosure can provide a technical solution to a technical problem associated with generating reliable, anatomically valid visualizations from user-driven instructions using large language models 144. In particular, conventional systems may generate visualization outputs or camera configurations directly from language model responses without verifying whether such outputs correspond to valid viewpoints within imaging data or satisfy anatomical, spatial, or physical constraints, thereby resulting in incorrect, misleading, or unusable visualizations. The apparatus 100 disclosed herein can address this problem by integrating large language model-generated camera configurations with a simulation and verification pipeline that evaluates proposed camera views against visualization criteria 124 derived from imaging data 112 and spatial constraints prior to output or actuation. By requiring simulated camera views 120 to satisfy visibility, feasibility, and anatomical relevance constraints before being displayed or used to control an imaging device 176, the processor 104 prevents propagation of invalid LLM outputs and ensures that only technically valid camera views 120 are presented or actuated. This approach improves the functioning of the visualization system itself by introducing a deterministic, data-driven validation layer that constrains generative model behavior using imaging-derived spatial representations, thereby reducing erroneous outputs, improving interpretability, and enhancing reliability of visualization control in anatomically complex environments.

With continued reference to FIG. 1, in some embodiments, the present disclosure may further provide a technical improvement to operation of a large language model 144 by introducing a feedback-controlled evaluation framework that governs whether LLM outputs 148 are permitted to be surfaced, revised, or suppressed. In such embodiments, rather than treating LLM outputs 148 as final or authoritative, the processor 104 may evaluate each LLM-generated proposed camera configuration 152 by simulating a corresponding camera view 120 and determining whether the simulated camera view 120 satisfies visualization criteria 124 grounded in imaging data 112 and spatial constraints. In some embodiments, when an LLM output 148 fails to satisfy the visualization criteria 124, the processor 104 may suppress output of the corresponding camera view 120 and invoke the LLM 144 to generate revised camera configurations 160, thereby enforcing a closed-loop refinement process. In some embodiments, this selective output mechanism may prevent propagation of incorrect, anatomically invalid, or physically unrealizable LLM outputs 148 and may condition the LLM 144 to operate within verifiable system constraints. In some embodiments, coupling generative reasoning with deterministic evaluation and rejection logic may enable the LLM 144 to iteratively converge toward outputs that are not only linguistically plausible but also technically valid and operationally executable within a visualization system.

Figure 2A:
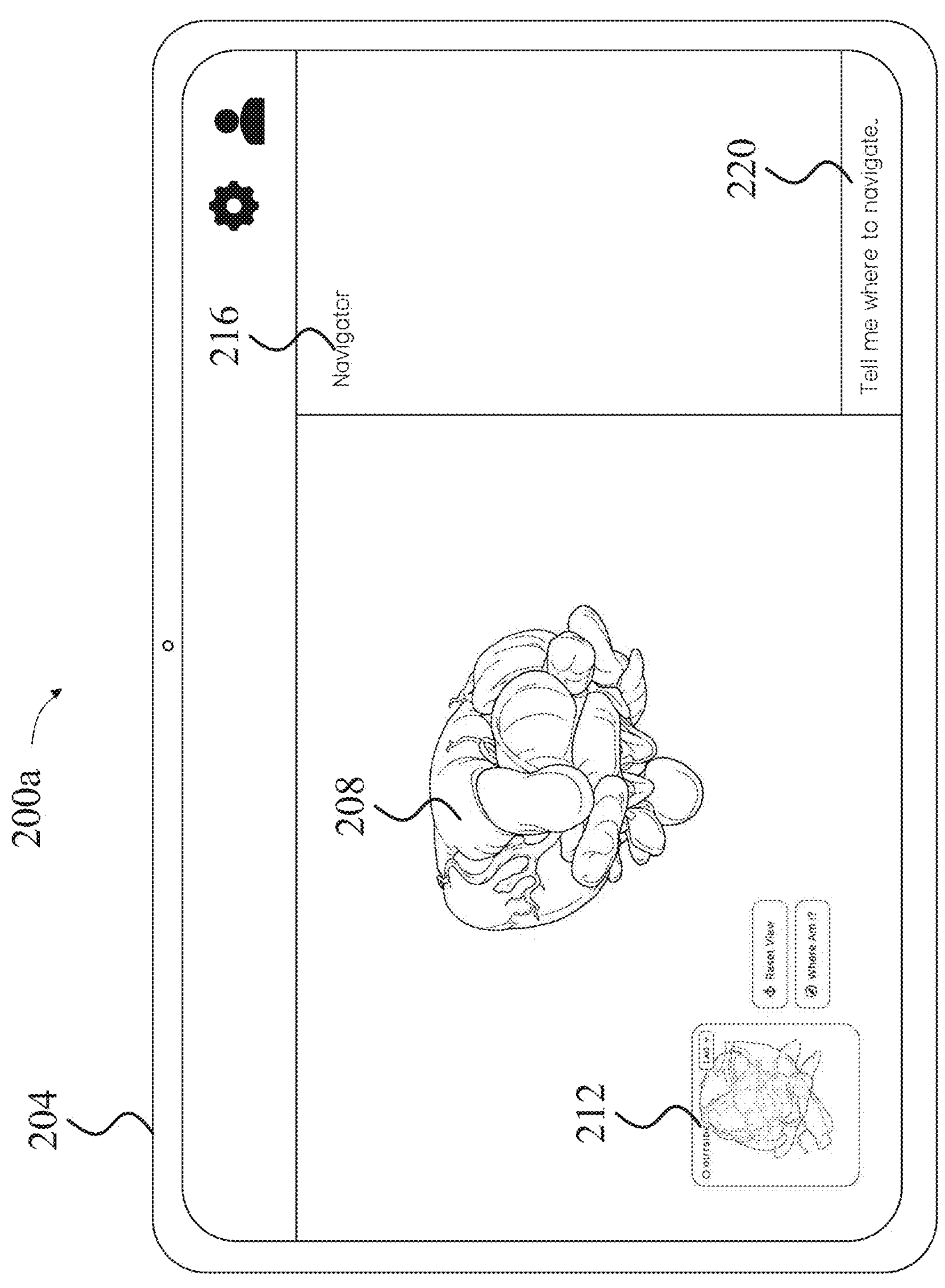
FIG. 2A illustrates an exemplary user interface.

Referring now to FIG. 2A, an exemplary user interface **200*a* is illustrated. In some embodiments, the user interface 200*a* may be presented on a display device 204. In some embodiments, the user interface 200*a* may be configured to visually present imaging data 208 corresponding to at least one anatomical structure. The imaging data 208 may be rendered within a primary visualization region of the display device 204 to provide a detailed three-dimensional view for inspection and navigation. In some embodiments, the user interface 200*a* may additionally present minimized imaging data 212, which may include a reduced-scale, thumbnail, overview, or contextual representation of the imaging data 208 that provides spatial orientation or navigational context relative to the primary visualization. In some embodiments, the user interface 200*a* may further include a navigator panel 216, which may also be referred to as a supplemental panel, auxiliary window, or secondary interaction region. In some cases, navigator panel 216 may be configured to present navigation controls, system status information, or guidance associated with traversing the imaging data 208. In some embodiments, the navigator panel 216 may include or be operatively coupled to an input field 220 configured to receive a user instruction, such as a natural-language navigation request, that directs how the imaging data 208 is to be visualized or navigated within the user interface 200***a*.

Figure 2B:
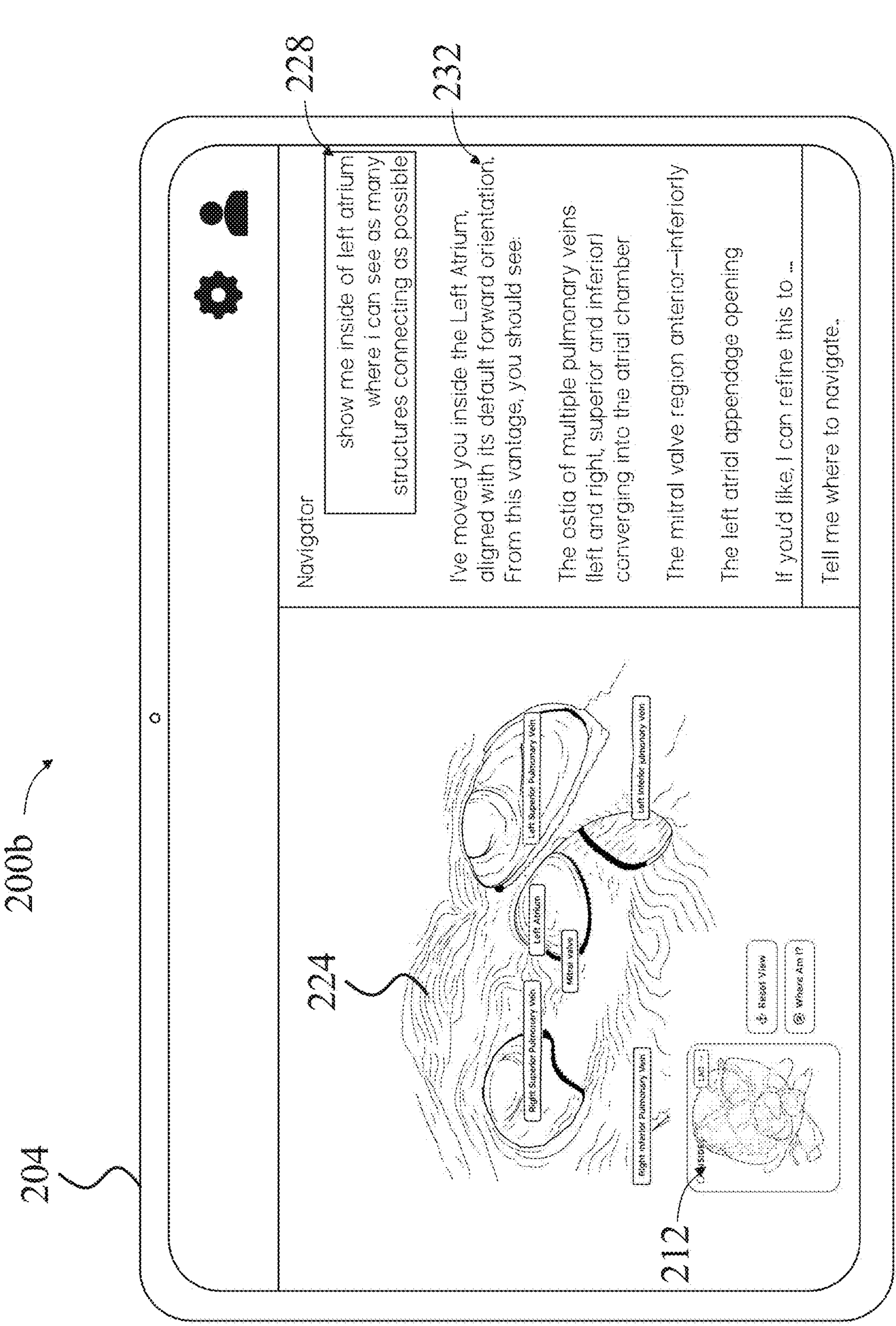
FIG. 2B illustrates another exemplary user interface.

Referring now to FIG. 2B, an exemplary user interface 200*b* is illustrated. In some embodiments, the user interface 200*b* may be presented on a display device 204. In some embodiments, the user interface 200*b* may be configured to display a camera view 224 corresponding to a visualization position within imaging data associated with an anatomical structure. The camera view 224 may represent a simulated or generated viewpoint determined as a function of a proposed camera configuration and may depict internal anatomical regions from a selected orientation and position. In some embodiments, the minimized imaging data 212 may be displayed within the user interface 200*b* as a reduced or thumbnail representation of the imaging data to provide global spatial context relative to the camera view 224. The minimized imaging data 212 may indicate a current navigation position, orientation, or region of interest within the anatomical structure while preserving display area for the primary camera view. In some embodiments, the user interface 200*b* may further receive a user instruction 228, such as a natural-language navigation or visualization request specifying a target anatomical region or viewing objective. In response to the user instruction 228, the user interface 200*b* may present an instruction response 232, which may include a textual explanation, confirmation of navigation actions taken, identification of visible anatomical features, or suggested follow-up instructions, thereby providing interactive feedback corresponding to the displayed camera view 224.

Figure 2C:
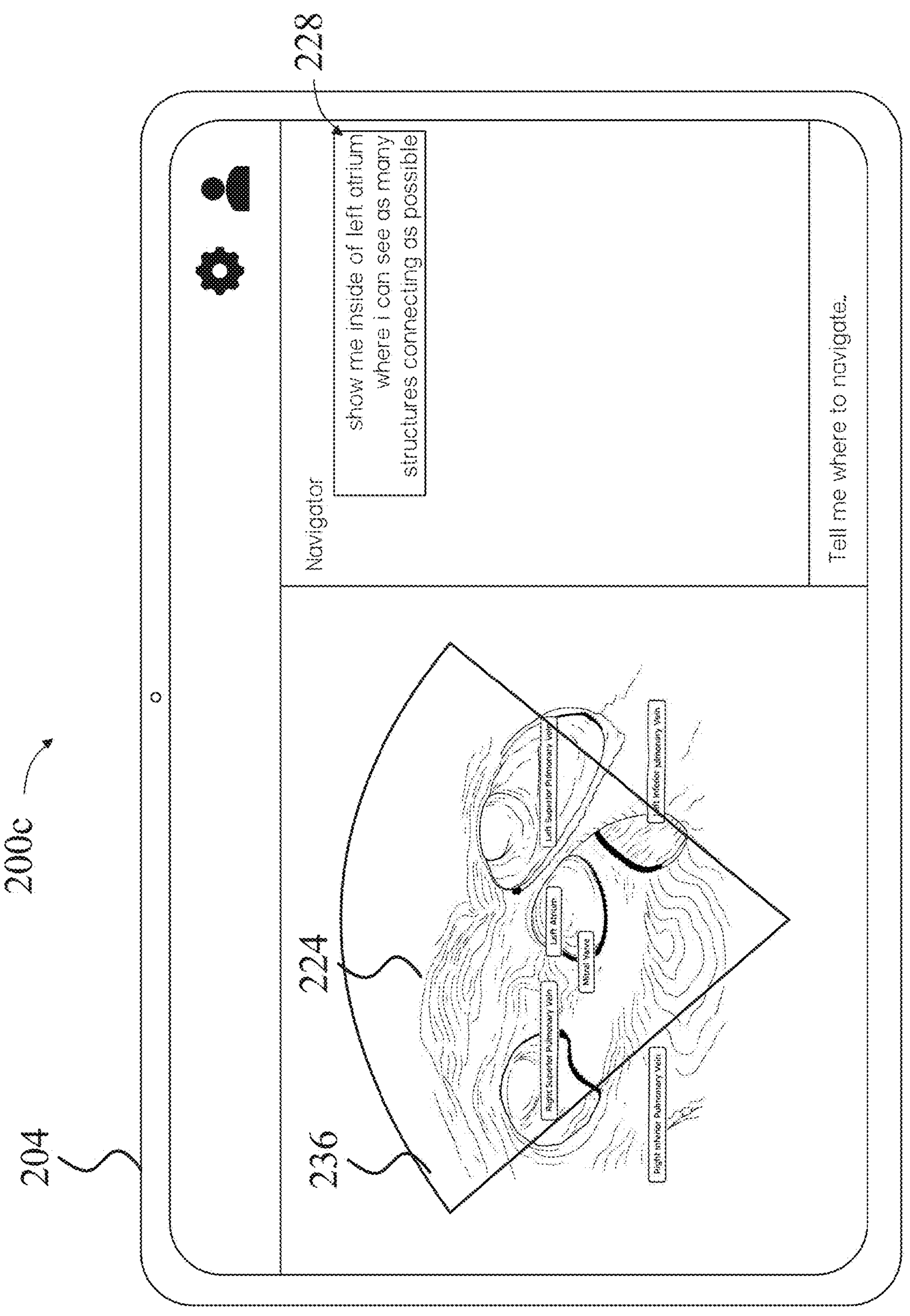
FIG. 2C illustrates an exemplary user interface including a field of view.

Referring now to FIG. 2C, an exemplary user interface 200*c* including a field of view 236 is illustrated. In some embodiments, the user interface 200*c* may display a camera view 224 corresponding to a simulated camera perspective of a three-dimensional anatomical structure. The user interface 200*c* may further include a user instruction 228, which may comprise a natural language request identifying at least one anatomical feature to be visualized. In some implementations, the system may parse the user instruction 228 to identify the at least one anatomical feature and determine one or more associated boundary regions of that feature within the anatomical model. The processor may then analyze visibility of the one or more boundary regions of the identified anatomical feature within the camera view 224 to determine whether the simulated camera view satisfies one or more visualization criteria. In certain embodiments, the one or more visualization criteria may include a requirement that the identified anatomical feature is present within the field of view 236 of the simulated camera view and, in some cases, that at least a portion of the boundary regions of the anatomical feature are visible within the camera view 224. Based on this analysis, the system may determine whether the simulated camera configuration satisfies the user instruction 228.

Figure 2D:
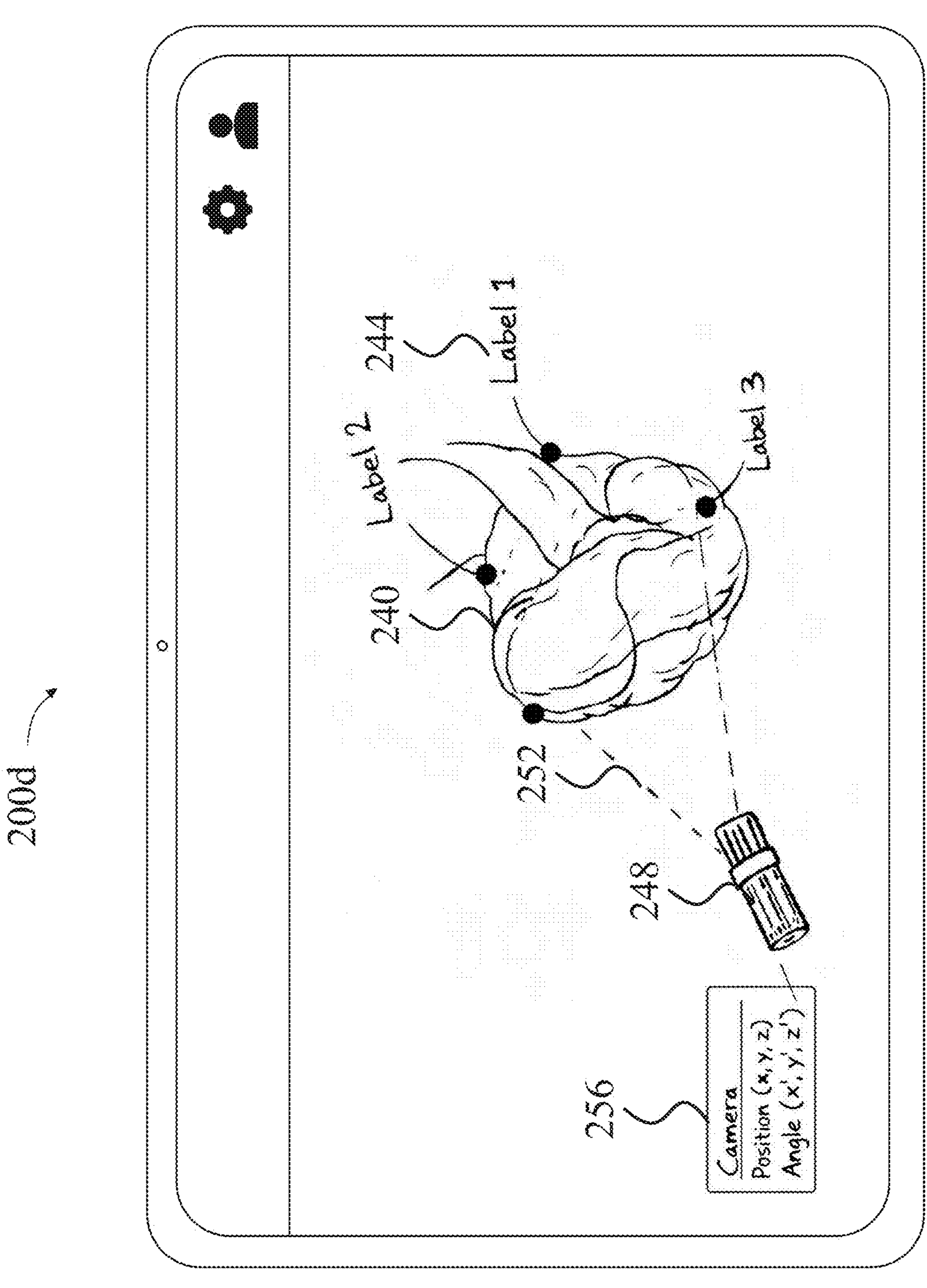
FIG. 2D illustrates an exemplary user interface including a camera cone.

Referring now to FIG. 2D, an exemplary user interface 200*d* including camera cone 252 corresponding to what the LLM is analyzing when determining whether the proposed camera configuration 256 satisfies the user request is illustrated. In some embodiments, the user interface 200*d* may display a three-dimensional mesh 240 representing an anatomical structure. The three-dimensional mesh 240 may include one or more presegmented labels 244 corresponding to identified anatomical features of the anatomical structure. A camera 248 may be positioned relative to the three-dimensional mesh 240. In some cases, the camera 248 may comprise a physical imaging device or a virtual camera defined within a three-dimensional rendering environment. A camera cone 252 may extend from the camera 248 to define a field of view associated with a particular perspective. A camera configuration 256 may define a position and orientation of the camera 248 or simulated view in three-dimensional space. In some cases, the camera configuration 256 may be generated in response to an output of a large language model (LLM) corresponding to a user instruction. The perspective defined by the camera 248 and the camera cone 252 may represent the viewpoint evaluated at this stage, such that the system analyzes the scene from the same spatial perspective that is proposed by the LLM. In some embodiments, the camera cone 252 may define a three-dimensional spatial volume extending from the camera 248, representing a geometric region of the three-dimensional mesh 240 that is within the camera's viewing frustum. The field of view 236 may correspond to a two-dimensional projection of at least a portion of the three-dimensional region defined by the camera cone 252, such that anatomical features contained within the camera cone 252 are rendered and visible within the field of view 236. To determine whether the returned camera configuration 256 contains at least part of the user request, the processor may compute an intersection between a region of the three-dimensional mesh 240 encompassed by the camera cone 252 and at least one of the presegmented labels 244 associated with an anatomical feature identified from the user instruction. For example, the system may determine whether at least a portion of the presegmented label 244 is spatially contained within the volume defined by the camera cone 252. If the intersection satisfies one or more visualization criteria, the camera configuration 256 may be accepted; otherwise, a revised camera configuration may be generated and re-evaluated.

Figure 3:
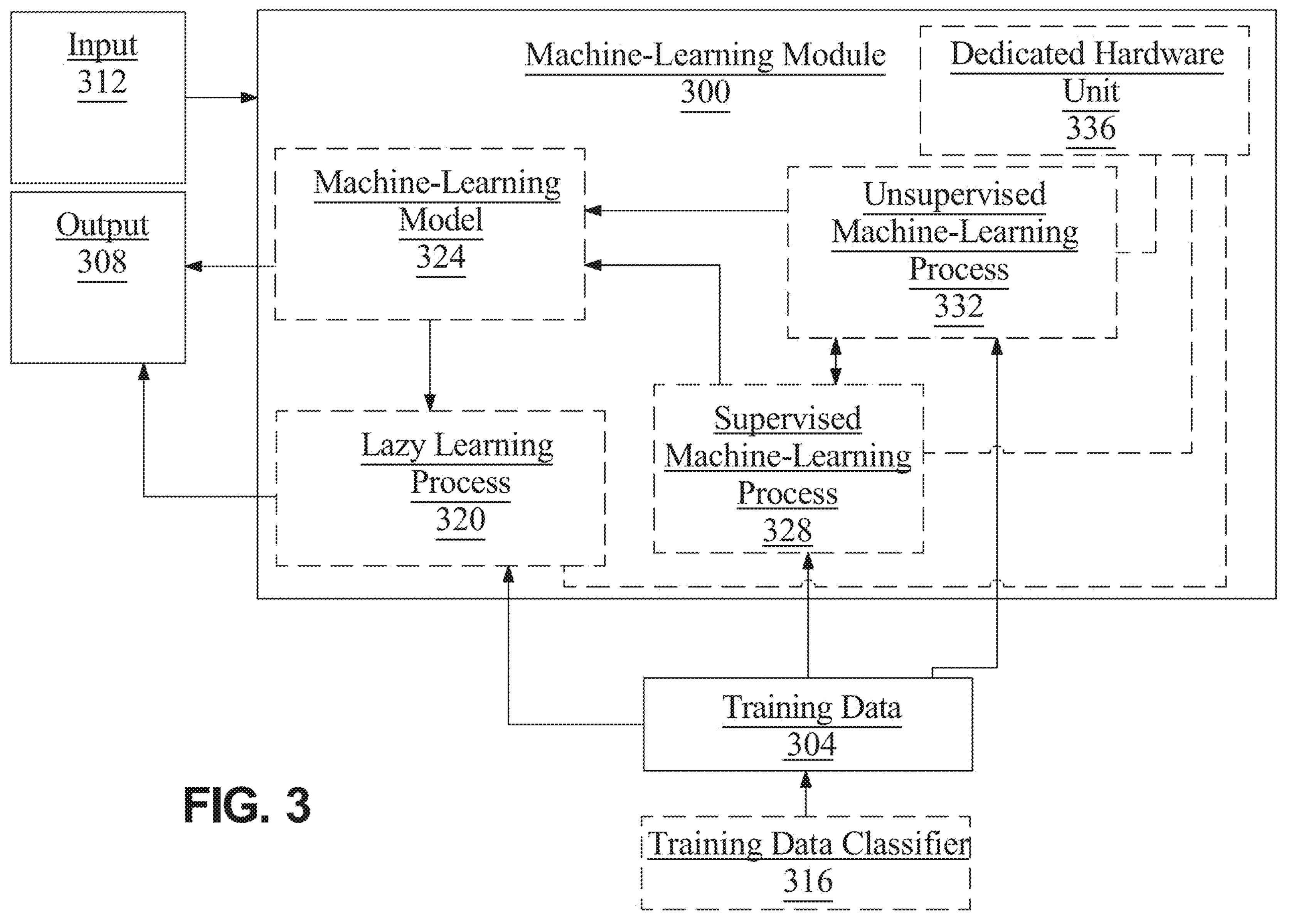
FIG. 3 illustrates a block diagram of an exemplary machine-learning module.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm instantiated in hardware or software logic, data structures, and/or functions that will be performed by a computing device/module to produce outputs 308 given data provided as inputs 312; this is in contrast to a non-machine learning software program where the commands to be executed are determined in advance by a user and written in a programming language.

Still referring to FIG. 3, "training data," as used herein, is data containing correlations that a machine-learning process may use to model relationships between two or more categories of data elements. For instance, and without limitation, training data 304 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure. As a non-limiting illustrative example, input data may include imaging data, user instruction, LLM output, camera view, revised camera configuration, anatomical structure, anatomical feature, spatial data, and the like. As a non-limiting illustrative example, output data may include LLM output, camera view, revised camera configuration, anatomical structure, anatomical feature, spatial data, instruction response, control signal, visualization objective, and the like.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 300 may generate a classifier using a classification algorithm, defined as a process whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to subject cohort related to subject demographics including age, gender, and the like, medical history, treatment history, and the like.

Still referring to FIG. 3, computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A)\ P(A)\div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 3, computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 3, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 3, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 3, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 3, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 3, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 3, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 3, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 3, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 3, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}: X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} = \frac{X - X_{mean}}{\sigma}.$$

Scaling may be performed using a median value of a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 3, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include imaging data, user instruction, LLM output, camera view, revised camera configuration, anatomical structure, anatomical feature, spatial data, and the like as described above as inputs, LLM output, camera view, revised camera configuration, anatomical structure, anatomical feature, spatial data, instruction response, control signal, visualization objective, and the like as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

With further reference to FIG. 3, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including, without limitation, gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 3, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 332 may not require a response variable; unsupervised processes 332 may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including, without limitation, support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 3, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 3, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 3, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 3, one or more processes or algorithms described above may be performed by at least a dedicated hardware unit 336. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 336 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 336 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 336 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 4:
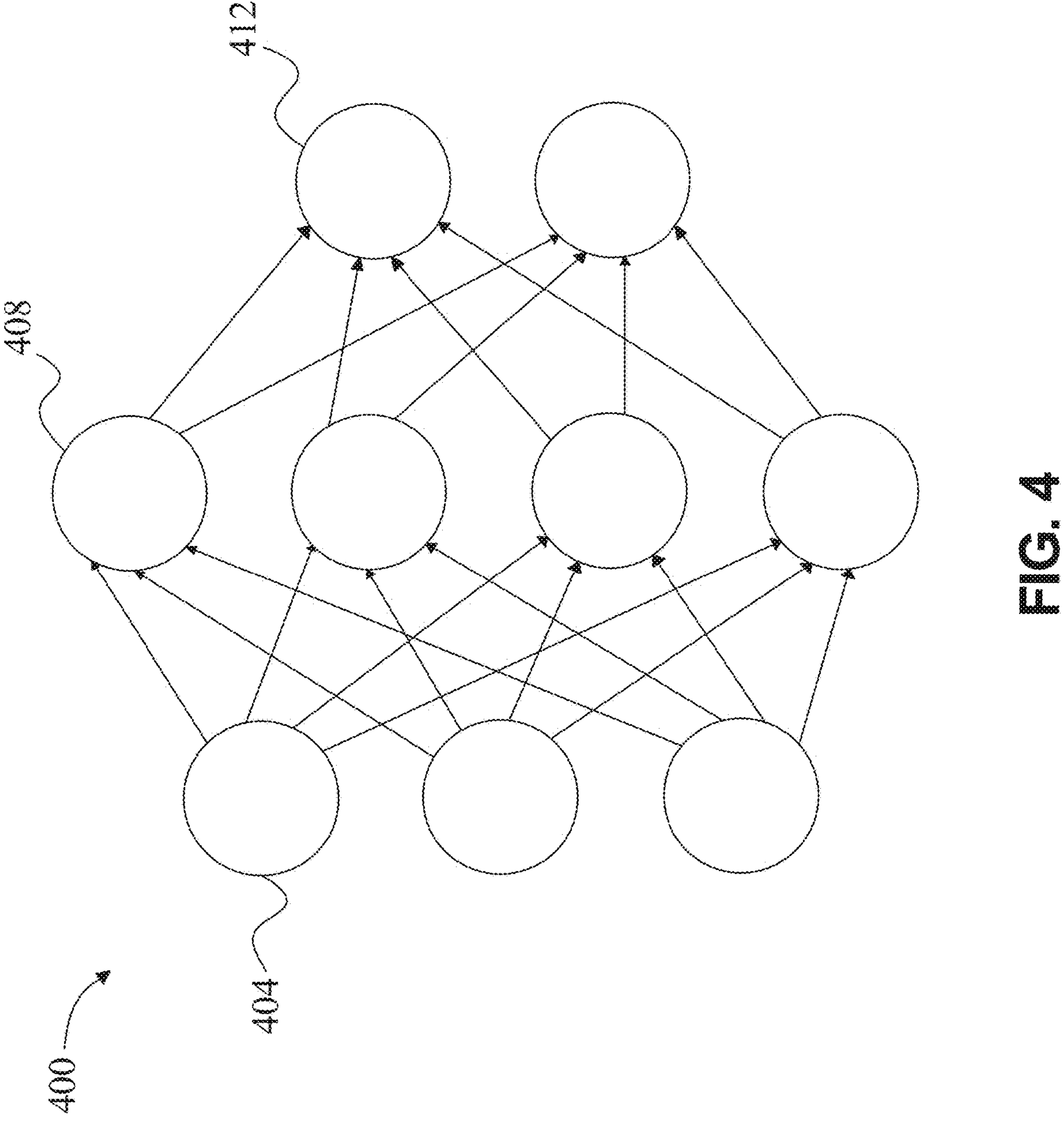
FIG. 4 illustrates a diagram of an exemplary neural network.

Referring now to FIG. 4, an exemplary embodiment of neural network 400 is illustrated. A neural network 400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
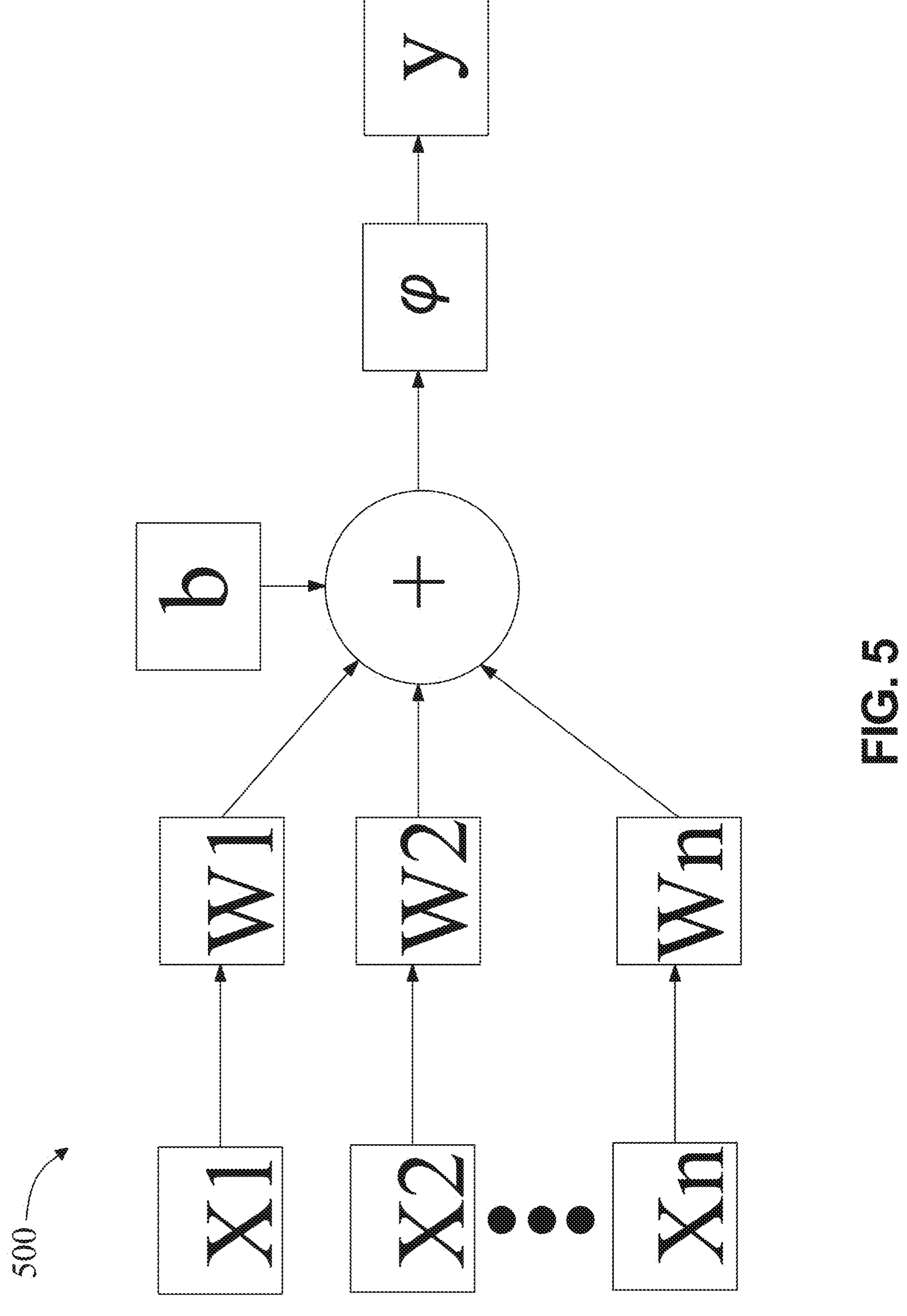
FIG. 5 illustrates a block diagram of an exemplary node in a neural network.

Referring now to FIG. 5, an exemplary embodiment of a node 500 of a neural network is illustrated. A node may include, without limitation, a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x \text{ for } x \geq 0 \\ \alpha(e^x - 1) \text{ for } x < 0 \end{cases}$$

for some value of α (this function may be replaced and/or weighted by its own derivative in some embodiments), a softmax function such as $$f(x_i) = \frac{e^x}{\Sigma_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$, or of other coefficients and/or parameters of an activation function, may be determined by training a neural network using training data, which may be performed using any suitable process as described above. Each weight in a neural network may, without limitation, be updated and/or tuned, based on an error function J, using a backpropagation updating method, such as:

$$w_{new} = w_{old} - \alpha\frac{dJ}{dw}$$

where $w_{new}$ is the updated weight value, $w_{old}$ is the previous weight value, α is a parameter to set the learning rate, and $$\frac{dJ}{dw}$$

is the partial derivative of with respect to weight w.

Figure 6A:
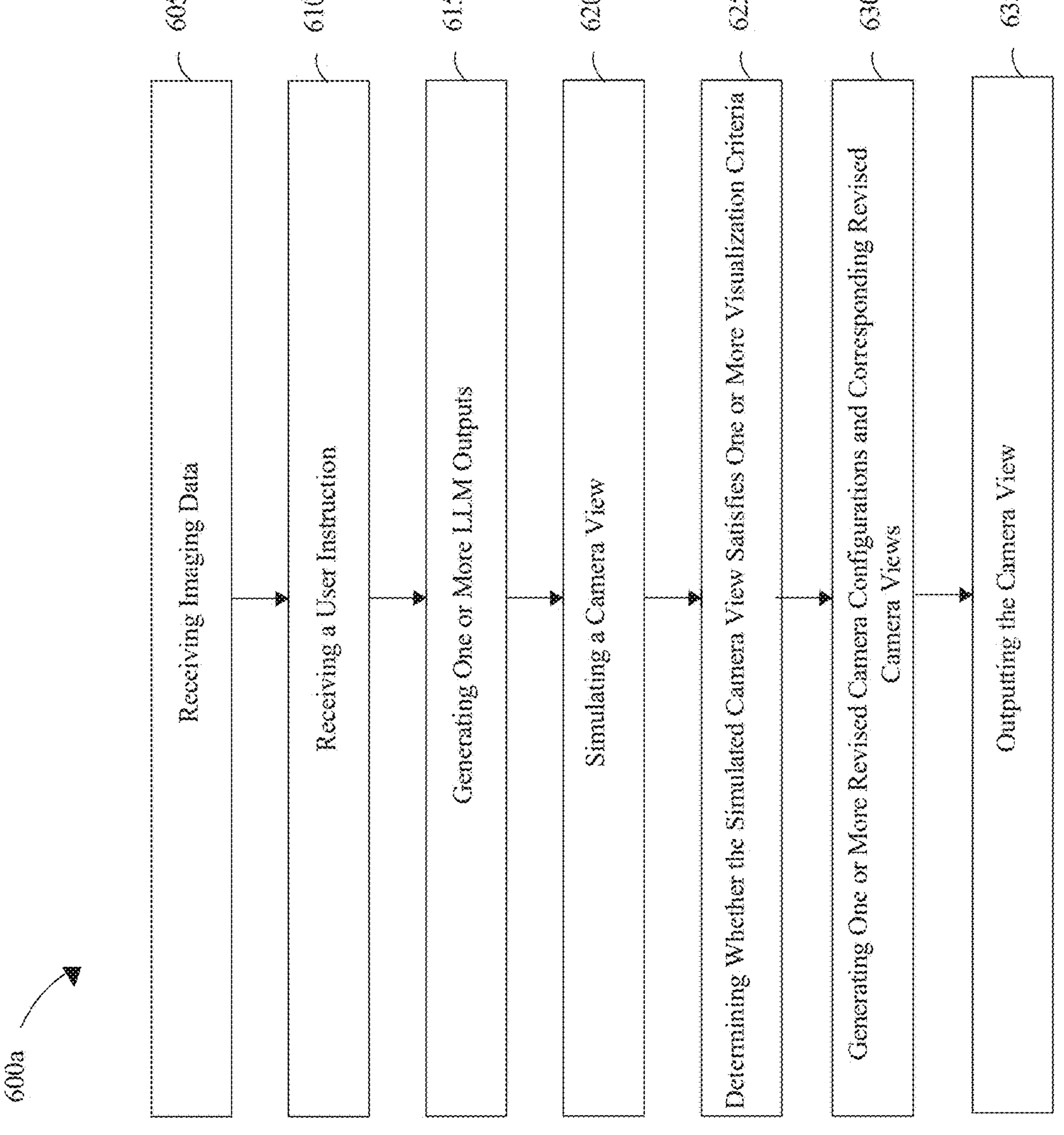
FIG. 6A illustrates a flow diagram of an exemplary method of controlling visualization of anatomical image data.

Referring now to FIG. 6A, a flow diagram of an exemplary method 600*a* of controlling visualization of anatomical image data. Method 600*a* contains a step 605 of receiving, using at least a processor, imaging data. In some embodiments, receiving the imaging data may include identifying one or more anatomical structures within the imaging data, generating spatial data as a function of the one or more anatomical structures, wherein the spatial data may include one or more segmented regions associated with one or more anatomical structures, and generating the one or more LLM outputs as a function of the user instruction and the spatial data. These may be implemented as described and with reference to FIGS. 1-5.

With continued reference to FIG. 6A, method 600*a* contains a step 610 of receiving, using at least a processor and through a user interface, a user instruction associated with imaging data. In some embodiments, receiving the user instruction may include evaluating, using the LLM, the user instruction to determine whether the user instruction defines a visualization configuration as a function of the spatial data, in response to determining that the user instruction does not define the visualization configuration, determining a visualization objective as a function of historical data associated with prior visualization configurations, and generating a revised user instruction as a function of the visualization objective. These may be implemented as described and with reference to FIGS. 1-5.

With continued reference to FIG. 6A, method 600*a* contains a step 615 of generating, using at least a processor and a large language model (LLM), one or more LLM outputs as a function of a user instruction and imaging data, wherein the one or more LLM outputs includes a proposed camera configuration. These may be implemented as described and with reference to FIGS. 1-5.

With continued reference to FIG. 6A, method 600*a* contains a step 620 of simulating, using at least a processor, a camera view as a function of a proposed camera configuration and imaging data. These may be implemented as described and with reference to FIGS. 1-5.

With continued reference to FIG. 6A, method 600*a* contains a step 625 of determining, using at least a processor, whether a simulated camera view satisfies one or more visualization criteria associated with a user instruction. In some cases, determining whether the simulated camera view satisfies the one or more visualization criteria may include providing the simulated camera view to the LLM and generating, using the LLM, an evaluation output indicating whether the simulated camera view satisfies the one or more visualization criteria. In some embodiments, determining whether the simulated camera view satisfies the one or more visualization criteria may include identifying at least one anatomical feature from the user instruction, and analyzing visibility of one or more boundary regions of the at least one anatomical feature within the simulated camera view, wherein the one or more visualization criteria include a requirement that the at least one anatomical feature associated with the user instruction is present within a field of view of the simulated camera view. In some embodiments, determining whether the simulated camera view satisfies the one or more visualization criteria may include determining whether the simulated camera view corresponds to a physically realizable camera position within a three-dimensional structure represented by the imaging data as a function of a spatial constraint associated with the three-dimensional structure. These may be implemented as described and with reference to FIGS. 1-5.

With continued reference to FIG. 6A, method 600*a* contains a step 630 of in response to determining that a simulated camera view does not satisfy one or more visualization criteria generating, using at least a processor and a LLM, one or more revised camera configurations and simulating, using the at least a processor, corresponding revised camera views as a function of the one or more revised camera configurations. In some embodiments, generating the one or more revised camera configurations may include iteratively generating the one or more revised camera configurations until at least one revised camera view satisfies the one or more visualization criteria, wherein the one or more revised camera views generated prior to satisfaction of the one or more visualization criteria are not output through the user interface. These may be implemented as described and with reference to FIGS. 1-5.

With continued reference to FIG. 6A, method 600*a* contains a step 635 of in response to determining that a simulated camera view satisfies one or more visualization criteria, outputting, using at least a processor, a camera view corresponding to a proposed camera configuration. In some embodiments, outputting the camera view may include modifying a visualization position of the imaging data associated with the camera view, and modifying the user interface to display the camera view and the imaging data in the modified visualization position. In some embodiments, outputting the camera view may include generating an instruction response as part of the one or more LLM outputs as a function of the user instruction and the simulated camera view, wherein the instruction response is generated after the simulated camera view satisfies the one or more visualization criteria, and modifying the user interface to display the instruction response concurrently with the camera view. In some embodiments, outputting the camera view may include generating a control signal as a function of the proposed camera configuration, and actuating an imaging device as a function of the control signal. These may be implemented as described and with reference to FIGS. 1-5.

Figure 6B:
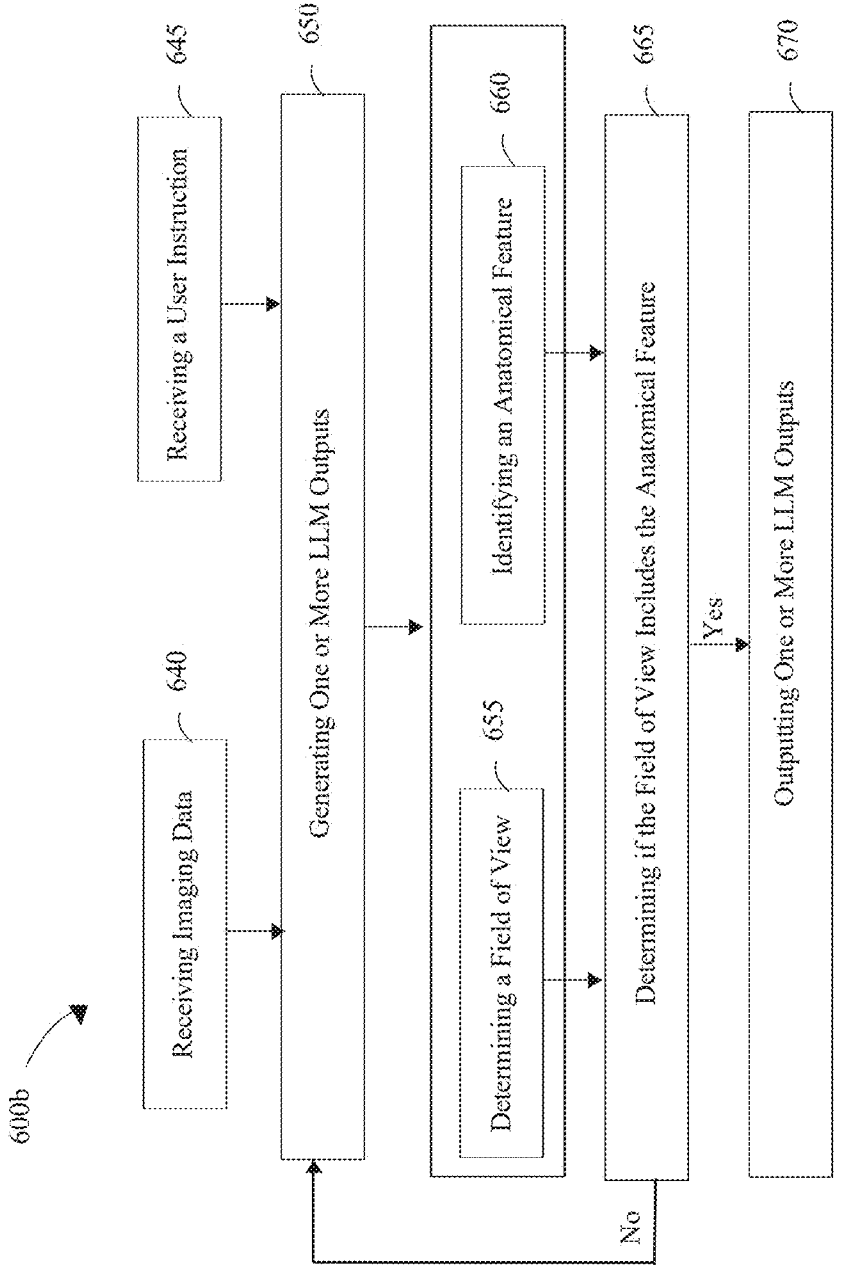
FIG. 6B illustrates a flow diagram of an exemplary method of using a large language model to output a large language model output.

Referring now to FIG. 6B, a flow diagram of an exemplary method 600*b* of using a large language model to output a large language model output is illustrated. In some cases, method 600*b* may include verifying whether a proposed camera configuration generated by a large language model includes at least a portion of a user-requested anatomical feature. Method 600*b* may be implemented using at least a processor and, in some embodiments, a large language model, as described herein with reference to FIGS. 1-6A.

With continued reference to FIG. 6B, method 600*b* contains a step 640 of receiving, using at least a processor, imaging data. In some embodiments, receiving the imaging data may include loading a three-dimensional representation of anatomical structures, including pre-segmented labels corresponding to one or more anatomical structures. In some embodiments, the imaging data may include spatial data defining segmented regions, boundary regions, or mesh representations associated with the anatomical structures. These may be implemented as described and with reference to FIGS. 1-6A.

With continued reference to FIG. 6B, method 600*b* contains a step 645 of receiving, using at least a processor and through a user interface, a user instruction associated with imaging data. In some embodiments, the user instruction may specify at least one anatomical feature or a visualization objective. In some embodiments, the user instruction may be processed to identify a target anatomical feature that is to be visualized within a field of view corresponding to a proposed camera configuration. These may be implemented as described and with reference to FIGS. 1-6A.

With continued reference to FIG. 6B, method 600*b* contains a step 650 of generating one or more LLM outputs, wherein the one or more LLM outputs include a proposed camera configuration. In some embodiments, the proposed camera configuration may include a camera position and a camera orientation corresponding to a field of view. In some embodiments, the LLM may generate the proposed camera configuration as a function of the user instruction and contextual information associated with the imaging data. These may be implemented as described and with reference to FIGS. 1-6A.

With continued reference to FIG. 6B, method 600*b* contains a step 655 of determining a field of view as a function of the proposed camera configuration. In some embodiments, determining the field of view may include generating a camera viewing volume, such as a camera cone or frustum, defined within a three-dimensional coordinate space associated with the imaging data. The field of view may represent a spatial region that is visible from the camera position under the camera orientation and field-of-view parameters. These may be implemented as described and with reference to FIGS. 1-6A.

With continued reference to FIG. 6B, method 600*b* contains a step 660 of identifying an anatomical feature associated with the user instruction. In some embodiments, identifying the anatomical feature may include mapping a term extracted from the user instruction to a corresponding pre-segmented anatomical label represented in the spatial data. In some embodiments, the anatomical feature may correspond to a segmented region, mesh representation, or boundary region associated with the imaging data. These may be implemented as described and with reference to FIGS. 1-6A.

With continued reference to FIG. 6B, method 600*b* contains a step 665 of determining whether the field of view includes the anatomical feature. In some embodiments, determining whether the field of view includes the anatomical feature may include intersecting the camera viewing volume with a three-dimensional representation of the pre-segmented anatomical label corresponding to the anatomical feature. In some embodiments, the processor may compute whether at least a portion of the segmented region or mesh associated with the anatomical feature lies within the field of view. In some embodiments, determining inclusion may include computing an intersection volume, surface overlap, or boundary coverage metric and comparing the metric to a threshold. If the anatomical feature is not included within the field of view, method 600*b* may return to step 650 to generate a revised proposed camera configuration. These may be implemented as described and with reference to FIGS. 1-6A.

With continued reference to FIG. 6B, method 600*b* contains a step 670 of outputting the LLM outputs in response to determining that the field of view includes the anatomical feature. In some embodiments, outputting the LLM outputs may include proceeding with visualization, simulation, or rendering of a camera view corresponding to the proposed camera configuration. In some embodiments, outputting may include modifying a user interface to present a camera view corresponding to the proposed camera configuration. These may be implemented as described and with reference to FIGS. 1-6A.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
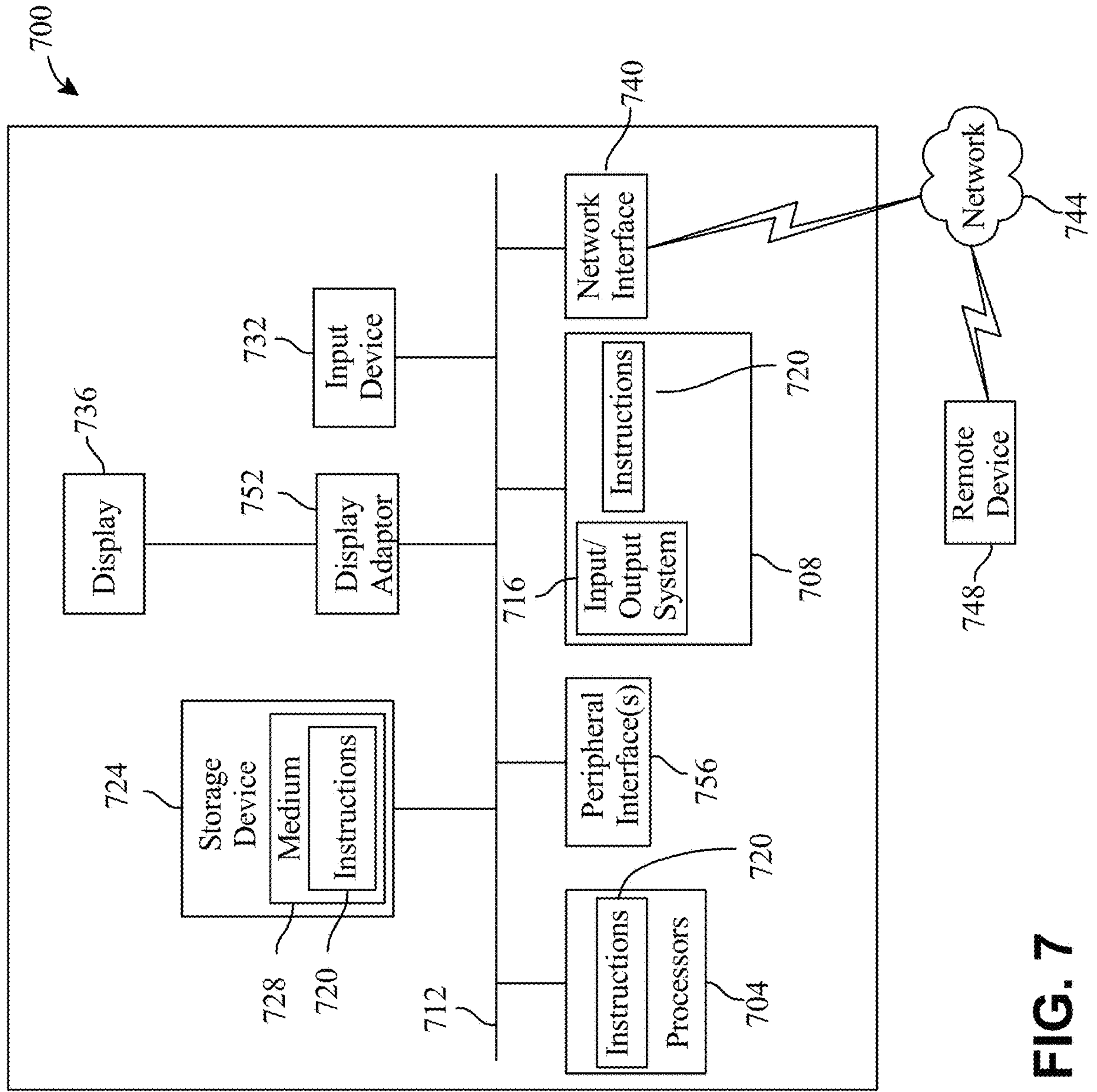
FIG. 7 illustrates a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC). Each processor and/or processor core may perform a state transition, instruction, and/or instruction step during a period of a "clock," or a regular oscillator that generates periodic output waveform, such as a square wave, having a regular period; different processors and/or cores may have distinct clocks. A processor may operate as and/or include a processing unit that performs instruction inputs, arithmetic operations, logical operations, memory retrieval operations, memory allocation operations, and/or input and output operations; a control circuit or module within a processor may determine which of the above-described functions a processor and/or unit within a processor will perform on a given clock cycle. A processor may include a plurality of processing units or "cores," each of which performs the above-described actions; multiple cores may work on disparate instruction sets and/or may work in parallel. A single core may also include multiple arithmetic, logic, or other units that can work in parallel with each other. Parallel computing between and/or within processors and/or cores may include multithreading processes and/or protocols such as without limitation Tomasulpo's algorithm. As used in this disclosure, "a processor," and/or "configuring a processor," is equivalent for the purposes of this disclosure to at least a processor, a plurality of processors, and/or a plurality of processor cores, and/or programming at least a processor, a plurality of processors, and/or a plurality of processor cores, which may be configured to operate on instructions in parallel and/or sequentially according to multithreading algorithms, parallel computing, load and/or task balancing, and/or virtualization, for instance and without limitation as described below.

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof. Memory 708 may include a primary memory and a secondary memory. "Primary memory," which may be implemented, without limitation as "random access memory" (RAM), is memory used for temporarily storing data for active use by a processor. In one or more embodiments, during use of the computing device, instructions and/or information may be transmitted to primary memory wherein information may be processed. In one or more embodiments, information may only be populated within primary memory while a particular software is running. In one or more embodiments, information within primary memory is wiped and/or removed after the computing device has been turned off and/or use of a software has been terminated. In one or more embodiments, primary memory may be referred to as "Volatile memory" wherein the volatile memory only holds information while data is being used and/or processed. In one or more embodiments, volatile memory may lose information after a loss of power.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In some embodiments, storage device 724 and/or devices "Secondary memory" also known as "storage," "hard disk drive" and the like for the purposes of this disclosure is a long-term storage device in which an operating system and other information is stored; operating system and/or main program instructions may alternatively or additionally be stored in hard-coded memory ROM, or the like. In one or more remote embodiments, information may be retrieved from secondary memory and copied to primary memory during use. In one or more embodiments, secondary memory may be referred to as non-volatile memory wherein information is preserved even during a loss of power. In some embodiments, data from secondary memory is transferred to primary memory before being accessed by a processor. In one or more embodiments, data is transferred from secondary to primary memory wherein circuitry may access the information from primary memory. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display 736. Examples of a display device include, but are not limited to, a liquid crystal display (LCD), a cathode ray tube (CRT), a plasma display, a light emitting diode (LED) display, and any combinations thereof. Display adapter 752 and display 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

Further referring to FIG. 7, a computing device may include any computing device as described in this disclosure, including without limitation a microcontroller, microprocessor, digital signal processor (DSP) and/or system on a chip (SoC) as described in this disclosure. A computing device may include, be included in, and/or communicate with a mobile device such as a mobile telephone or smartphone. A computing device may include a single device having components as described above operating independently or may include two or more such devices and/or components thereof operating in concert, in parallel, sequentially or the like; two or more devices, processors, memory elements, and the like may be included together in a single computing device or in two or more computing devices. A computing device may interface or communicate with one or more additional devices as described below in further detail via a network interface device.

In some embodiments, and still referring to FIG. 7, a computing device may be a component of a combination of at least a computing device; at least a computing device may include, as a non-limiting example, a first computing device or cluster of computing devices in a first location and a second computing device or cluster of computing devices in a second location. At least a computing device may include one or more computing devices dedicated to data storage, security, distribution of traffic for load balancing, and the like. At least a computing device may distribute one or more computing tasks as described below across a plurality of computing devices of computing device, which may operate in parallel, in series, redundantly, or in any other manner used for distribution of tasks or memory between computing devices. At least a computing device may be implemented, as a non-limiting example, using a "shared nothing" architecture.

With continued reference to FIG. 7, one or more programs or software instructions may include a principal program and/or operating system; principal program and/or operating system may be a program that runs automatically upon startup of a computing device and manages computer hardware and software resources. Principal program and/or operating system may include "startup," "loop," and/or "main" programs on a microcontroller; such programs may initialize hardware resources and subsequently iterate through a series of instructions to make function calls, read in data at input ports, output data at output ports, and process interrupts caused by asynchronous data inputs or the like. Principal program and/or operating system may include, without limitation, an operating system, which may schedule program tasks to be implemented by one or more processors, act as an intermediary between one or more programs and inputs, outputs, hardware and/or memory. Examples of operating systems include without limitation Unix, Linux, Microsoft Windows, Android, Disc Operating System (DOS) and the like. Operating systems may include, without limitation, multi-computer operating systems that run across multiple computing devices, real-time operating systems, and hypervisors. A "hypervisor," as used in this disclosure, is an operating system that runs a virtual machine and/or container, where virtual machines and/or containers create virtual interfaces for programs that mimic the behavior of hardware elements such as processors and/or memory; interactions with such virtual interfaces appear, to programs executed on virtual machines, to function as interactions with physical hardware, while in reality the hypervisor and/or programs such as containers (1) receive inputs from programs to the virtual resources and allocate such inputs to physical hardware that is not directly accessible to the programs, and (2) receive outputs from physical hardware and transmit such outputs to the programs in the form of apparent outputs from the virtual hardware. In some cases, one or more of computing system 700, processor 704, and memory 708 may be virtualized; that is, a virtual machine and/or container may interact directly with such computing system 700, processor 704, and/or memory 708, while managing communications therefrom and thereto via a virtual interface with programs. Computer virtualization may include dividing, or augmenting computing resources into a virtual machine, operating system, processor, and/or container. Virtualization of computer resources may be implemented through use of (1) multiple components, or portions thereof, working in concert, as if they were one unified (virtual) component; and/or (2) a portion of one or more components working as though it were a complete (virtual) component. For instance, where processor 704 comprises a plurality of processors and/or processor cores, virtualization may, in some cases, simulate or emulate a single (virtual) processor whose functions are allocated to one or more of the plurality of processors and/or processor cores. In this case, while processor 704 may be said to be virtualized, the processor 704, nevertheless, comprises actual hardware processor(s) or portion(s) thereof. Accordingly, in this disclosure, where a processor is said to perform instructions, such processor may comprise a virtualized processor, comprising a plurality or portion of hardware processors. Likewise, in this disclosure, where a memory is said to contain (i.e., store) instructions, such memory may comprise a virtualized memory, comprising a plurality or portion of memories. Technologies that enable such virtualization include (1) QEMU; (2) VMware by Broadcom Inc of Palo Alto, California; (3) VirtualBox by Oracle Corporation headquartered in Austin, Texas; and (4) kernel-based virtual machine (KVM).

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods and apparatuses according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for controlling visualization of anatomical image data, the apparatus comprising:

at least a processor; and a memory communicatively connected to the at least a processor, wherein the memory contains instructions configuring the at least a processor to:

receive imaging data;

receive, through a user interface, a user instruction associated with the imaging data;

generate, using a large language model (LLM), one or more LLM outputs as a function of the user instruction and the imaging data, wherein the one or more LLM outputs comprises a proposed camera configuration;

simulate a camera view as a function of the proposed camera configuration and the imaging data;

determine whether the simulated camera view satisfies one or more visualization criteria associated with the user instruction;

in response to determining that the simulated camera view does not satisfy the one or more visualization criteria:

generate, using the LLM, one or more revised camera configurations; and simulate corresponding revised camera views as a function of the one or more revised camera configurations; and in response to determining that the simulated camera view satisfies the one or more visualization criteria, output the camera view corresponding to the proposed camera configuration.

2. The apparatus of claim 1, wherein receiving the imaging data comprises:

identifying one or more anatomical structures within the imaging data;

generating spatial data as a function of the one or more anatomical structures, wherein the spatial data comprises one or more segmented regions associated with the one or more anatomical structures; and generating the one or more LLM outputs as a function of the user instruction and the spatial data.

3. The apparatus of claim 2, wherein receiving the user instruction comprises:

evaluating, using the LLM, the user instruction to determine whether the user instruction defines a visualization configuration as a function of the spatial data;

in response to determining that the user instruction does not define the visualization configuration, determining a visualization objective as a function of historical data associated with prior visualization configurations; and generating a revised user instruction as a function of the visualization objective.

4. The apparatus of claim 1, wherein determining whether the simulated camera view satisfies the one or more visualization criteria comprises:

providing the simulated camera view to the LLM; and generating, using the LLM, an evaluation output indicating whether the simulated camera view satisfies the one or more visualization criteria.

5. The apparatus of claim 1, wherein determining whether the simulated camera view satisfies the one or more visualization criteria comprises:

identifying at least one anatomical feature from the user instruction; and analyzing visibility of one or more boundary regions of the at least one anatomical feature within the simulated camera view, wherein the one or more visualization criteria comprise a requirement that the at least one anatomical feature associated with the user instruction is present within a field of view of the simulated camera view.

6. The apparatus of claim 1, wherein determining whether the simulated camera view satisfies the one or more visualization criteria comprises determining whether the simulated camera view corresponds to a physically realizable camera position within a three-dimensional structure represented by the imaging data as a function of a spatial constraint associated with the three-dimensional structure.

7. The apparatus of claim 1, wherein generating the one or more revised camera configurations comprises iteratively generating the one or more revised camera configurations until at least one revised camera view satisfies the one or more visualization criteria, wherein the one or more revised camera views generated prior to satisfaction of the one or more visualization criteria are not output through the user interface.

8. The apparatus of claim 1, wherein outputting the camera view comprises:

modifying a visualization position of the imaging data associated with the camera view; and modifying the user interface to display the camera view and the imaging data in the modified visualization position.

9. The apparatus of claim 1, wherein outputting the camera view comprises:

generating an instruction response as part of the one or more LLM outputs as a function of the user instruction and the simulated camera view, wherein the instruction response is generated after the simulated camera view satisfies the one or more visualization criteria; and modifying the user interface to display the instruction response concurrently with the camera view.

10. The apparatus of claim 1, wherein outputting the camera view comprises:

generating a control signal as a function of the proposed camera configuration; and actuating an imaging device as a function of the control signal.

11. A method of controlling visualization of anatomical image data, the method comprising:

receiving, using at least a processor, imaging data;

receiving, using the at least a processor and through a user interface, a user instruction associated with the imaging data;

generating, using the at least a processor and a large language model (LLM), one or more LLM outputs as a function of the user instruction and the imaging data, wherein the one or more LLM outputs comprises a proposed camera configuration;

simulating, using the at least a processor, a camera view as a function of the proposed camera configuration and the imaging data;

determining, using the at least a processor, whether the simulated camera view satisfies one or more visualization criteria associated with the user instruction;

in response to determining that the simulated camera view does not satisfy the one or more visualization criteria:

generating, using the at least a processor and the LLM, one or more revised camera configurations; and simulating, using the at least a processor, corresponding revised camera views as a function of the one or more revised camera configurations; and in response to determining that the simulated camera view satisfies the one or more visualization criteria, outputting, using the at least a processor, the camera view corresponding to the proposed camera configuration.

12. The method of claim 11, wherein receiving the imaging data comprises:

identifying one or more anatomical structures within the imaging data;

generating spatial data as a function of the one or more anatomical structures, wherein the spatial data comprises one or more segmented regions associated with the one or more anatomical structures; and generating the one or more LLM outputs as a function of the user instruction and the spatial data.

13. The method of claim 12, wherein receiving the user instruction comprises:

evaluating, using the LLM, the user instruction to determine whether the user instruction defines a visualization configuration as a function of the spatial data;

in response to determining that the user instruction does not define the visualization configuration, determining a visualization objective as a function of historical data associated with prior visualization configurations; and generating a revised user instruction as a function of the visualization objective.

14. The method of claim 11, wherein determining whether the simulated camera view satisfies the one or more visualization criteria comprises:

providing the simulated camera view to the LLM; and generating, using the LLM, an evaluation output indicating whether the simulated camera view satisfies the one or more visualization criteria.

15. The method of claim 11, wherein determining whether the simulated camera view satisfies the one or more visualization criteria comprises:

identifying at least one anatomical feature from the user instruction; and analyzing visibility of one or more boundary regions of the at least one anatomical feature within the simulated camera view, wherein the one or more visualization criteria comprise a requirement that the at least one anatomical feature associated with the user instruction is present within a field of view of the simulated camera view.

16. The method of claim 11, wherein determining whether the simulated camera view satisfies the one or more visualization criteria comprises determining whether the simulated camera view corresponds to a physically realizable camera position within a three-dimensional structure represented by the imaging data as a function of a spatial constraint associated with the three-dimensional structure.

17. The method of claim 11, wherein generating the one or more revised camera configurations comprises iteratively generating the one or more revised camera configurations until at least one revised camera view satisfies the one or more visualization criteria, wherein the one or more revised camera views generated prior to satisfaction of the one or more visualization criteria are not output through the user interface.

18. The method of claim 11, wherein outputting the camera view comprises:

modifying a visualization position of the imaging data associated with the camera view; and modifying the user interface to display the camera view and the imaging data in the modified visualization position.

19. The method of claim 11, wherein outputting the camera view comprises:

generating an instruction response as part of the one or more LLM outputs as a function of the user instruction and the simulated camera view, wherein the instruction response is generated after the simulated camera view satisfies the one or more visualization criteria; and modifying the user interface to display the instruction response concurrently with the camera view.

20. The method of claim 11, wherein outputting the camera view comprises:

generating a control signal as a function of the proposed camera configuration; and actuating an imaging device as a function of the control signal.

* * * * *